(12) United States Patent
Lee et al.

(10) Patent No.: US 10,265,024 B2
(45) Date of Patent: Apr. 23, 2019

(54) SENSOR SYSTEM FOR HEART RATE MEASUREMENT PER AXIS OF SHARED ORIENTATION

(71) Applicant: Salutron, Inc., Fremont, CA (US)

(72) Inventors: Yong Jin Lee, Palo Alto, CA (US); Lino Velo, San Ramon, CA (US)

(73) Assignee: Salutron, Inc., Newark, CA (US)

( * ) Notice: Subject to any disclaimer, the term of this patent is extended or adjusted under 35 U.S.C. 154(b) by 542 days.

(21) Appl. No.: 14/341,803

(22) Filed: Jul. 26, 2014

(65) Prior Publication Data

US 2016/0022220 A1 Jan. 28, 2016

(51) Int. Cl.
*A61B 5/00* (2006.01)
*A61B 5/024* (2006.01)
*A61B 5/11* (2006.01)

(52) U.S. Cl.
CPC .......... *A61B 5/721* (2013.01); *A61B 5/02433* (2013.01); *A61B 5/02438* (2013.01); *A61B 5/1118* (2013.01); *A61B 5/681* (2013.01); *A61B 2562/0219* (2013.01)

(58) Field of Classification Search
None
See application file for complete search history.

(56) References Cited

U.S. PATENT DOCUMENTS

| | | | |
|---|---|---|---|
| 8,032,206 B1 | 10/2011 | Farazi et al. | |
| 8,512,240 B1 | 8/2013 | Zuckerman-Stark et al. | |
| 8,545,417 B2 | 10/2013 | Banet et al. | |
| 8,622,922 B2 | 1/2014 | Banet et al. | |
| 2002/0188210 A1* | 12/2002 | Aizawa | A61B 5/02433 600/503 |
| 2009/0112104 A1* | 4/2009 | Usuda | A61B 5/02116 600/494 |

(Continued)

FOREIGN PATENT DOCUMENTS

JP 2002-224059 * 8/2002
WO 2013042070 A1 3/2013

OTHER PUBLICATIONS

English translation of JP 2002-224059, provided by machine translation tool J-PLAT-PAT.*

(Continued)

*Primary Examiner* — Katherine L Fernandez
(74) *Attorney, Agent, or Firm* — Vierra Magen Marcus LLP

(57) ABSTRACT

Technology is described for a wearable sensor system including an accelerometer and a PPG optical sensor having light processing elements including at least one photodetector in at least one linear configuration sharing an axis of orientation with the accelerometer. Heart rate measurements determined from reflected light detected by a photodetector of the light processing elements in a linear configuration are co-sampled with accelerometer measurements for one of its axes sharing its orientation with the linear configuration, thus providing per axis measurements which provide more precise data points for more easily compensating for motion artifacts in heart rate data. A wrist wearable biometric monitoring device is also described which embodies the wearable sensor system and performs active motion artifact compensation.

13 Claims, 14 Drawing Sheets

(56) References Cited

U.S. PATENT DOCUMENTS

2010/0113948 A1* 5/2010 Yang .................. A61B 5/02416
                                                        600/500
2012/0203080 A1* 8/2012 Kim .................. A61B 5/02416
                                                        600/301

OTHER PUBLICATIONS

Kuboyama, Yuta, Motion Artifact Cancellation for Wearable Photoplethysmographic Sensor, published by the Massachusetts Institute of Technology, 2010, 66 pages. Retrieved from the Internet [online] Apr. 7, 2015 http://dspace.mit.edu/bitstream/handle/1721.1/61168/699492105.pdf?seguence=1 at which searchable copy is located.

* cited by examiner

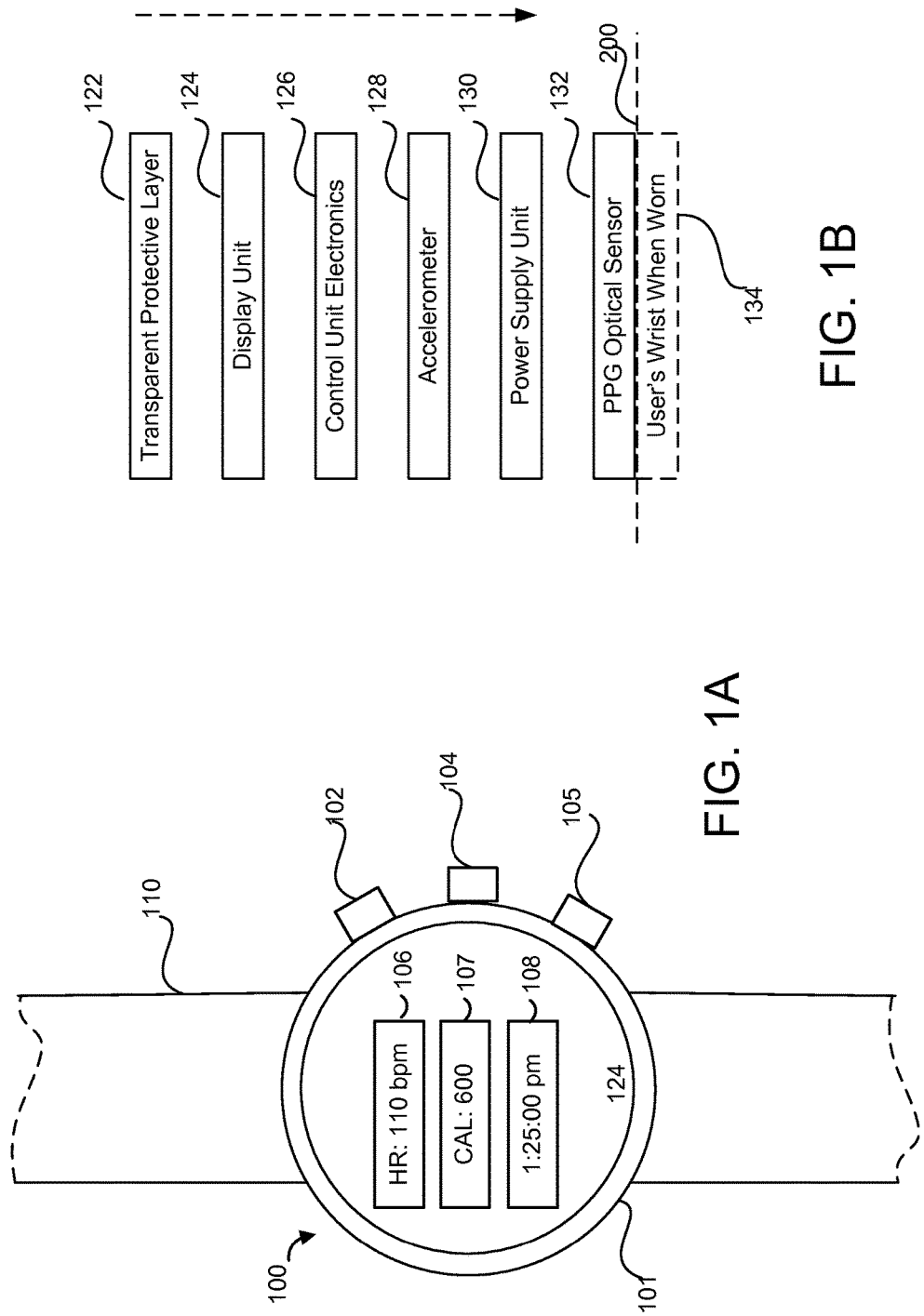

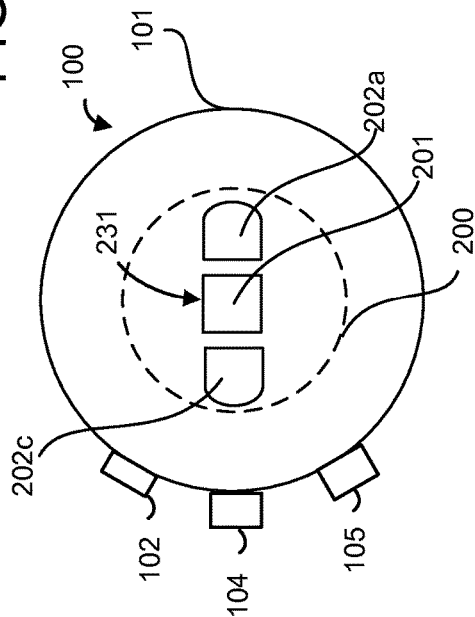
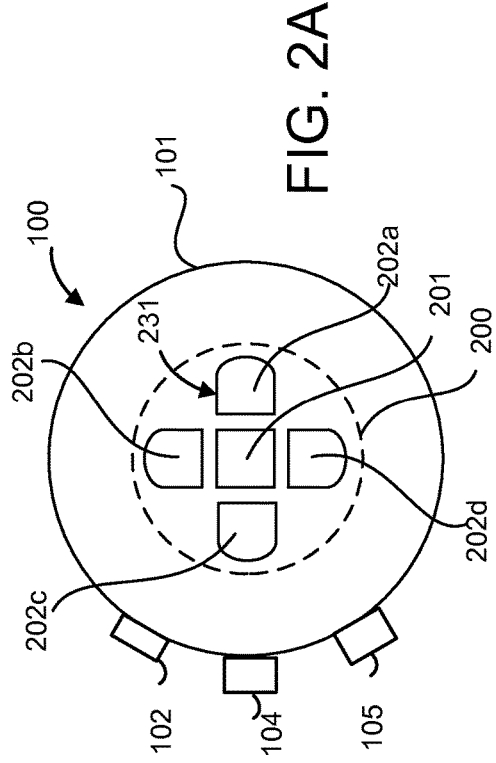
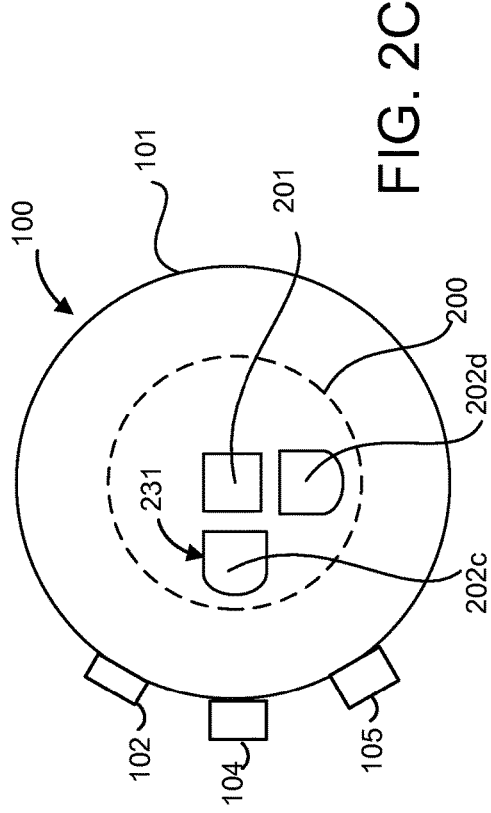

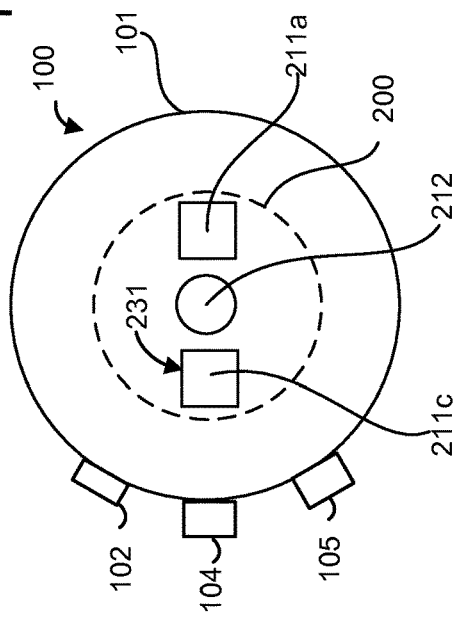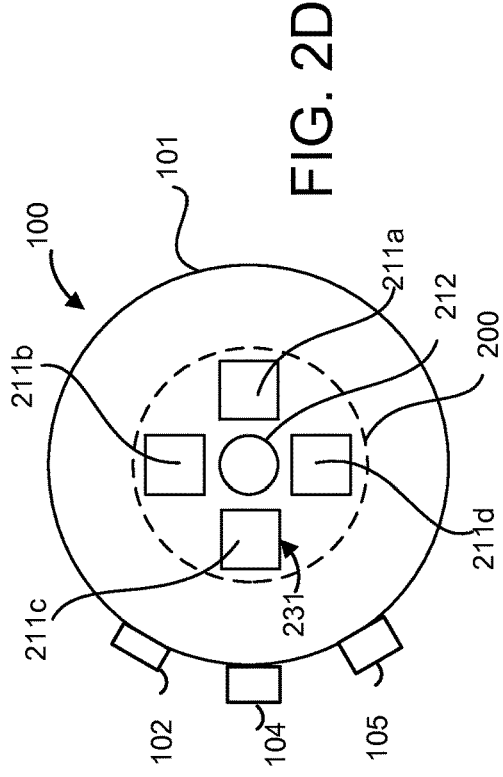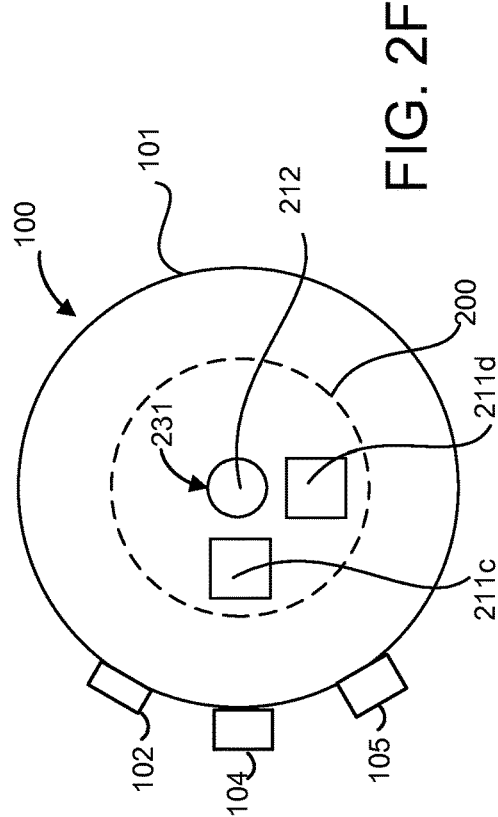

SENSOR SYSTEM FOR HEART RATE MEASUREMENT PER AXIS OF SHARED ORIENTATION

BACKGROUND

Activity monitors have become popular tools for promoting exercise and a healthy lifestyle. An activity monitor may include a Photoplethysmography (PPG) sensor which provides data from which heart rate can be determined. PPG is an optical measurement technique in which light is directed towards the skin, and changes in blood volume pulsing under the skin are correlated to changes in reflected light. Accurate heart rate data is a desired goal. However, motion of the user during an activity like walking, running, swimming or biking can create motion artifact data in the same frequency range, e.g. beats per minute, as expected for the heart rate data from the sensor, thus adversely affecting heart rate data accuracy.

SUMMARY

The technology provides for one or more embodiments of a wearable sensor system for providing heart rate measurement per axis of orientation shared between a linear configuration of light processing elements of a photoplethysmography (PPG) optical sensor and an accelerometer. One embodiment comprises an accelerometer for providing accelerometer measurements for at least one accelerometer axis of orientation and a PPG optical sensor having at least one linear configuration of light processing elements. The embodiment also comprises a housing for supporting and positioning the accelerometer and the at least one linear configuration of light processing elements of the PPG optical sensor for the linear configuration to share the orientation of the at least one accelerometer axis of orientation.

Additionally, the housing has a surface with one or more light pass-through sections forming at least one linear configuration matching the at least one linear configuration of the light processing elements. The housing aligns the light processing elements with the one or more light pass-through sections. The surface with the one or more light pass-through sections is in contact with skin when the wearable sensor system is worn.

The technology provides for one or more embodiments of a method for active motion artifact compensation of heart rate data based on measurements taken for at least one axis of orientation shared by light processing elements of a PPG optical sensor and an accelerometer. An embodiment of the method comprises obtaining co-sampled accelerometer measurement data and PPG measurement data for at least one axis of orientation shared by the accelerometer and light processing elements of the PPG optical sensor. The co-sampled accelerometer measurement data for the at least one shared axis of orientation is transformed into motion data defined in terms of one or more reference parameters, and the co-sampled PPG measurement data for the at least one shared axis of orientation is transformed into heart rate data defined in terms of the same one or more reference parameters.

The embodiment of the method further comprises identifying any data point of the motion data and any data point of the heart rate data for the at least one shared axis of orientation that satisfy matching criteria. Motion artifact compensated heart rate data is created by discarding any data point of the heart rate data identified as satisfying the matching criteria.

The technology also provides for one or more embodiments of a wrist wearable biometric monitoring device. An embodiment of a wrist wearable biometric monitoring device comprises an accelerometer for providing accelerometer measurements for at least one accelerometer axis of orientation and a PPG optical sensor having at least one linear configuration of light processing elements. Additionally, the embodiment comprises a housing for supporting and positioning the accelerometer and the at least one linear configuration of light processing elements of the PPG optical sensor for the linear configuration to share the orientation of the at least one accelerometer axis of orientation. The housing has a surface with one or more light pass-through sections forming at least one linear configuration matching the at least one linear configuration of the light processing elements. The housing aligns the light processing elements with the one or more light pass-through sections. The surface with the one or more light pass-through sections is in contact with skin when the wrist wearable biometric monitoring device is worn.

The embodiment of the wrist wearable biometric monitoring device further comprises one or more processors communicatively coupled to the accelerometer and the PPG optical sensor for performing active motion artifact compensation of heart rate data based on measurements taken for at least one axis of orientation shared by the light processing elements of the PPG optical sensor and the accelerometer.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

FIG. 1A illustrates a top view of an embodiment of a wrist wearable biometric monitoring device including a PPG optical sensor and an accelerometer, each providing measurements for an axis of shared orientation.

FIG. 1B illustrates an example of an arrangement of different layers of hardware supported by a housing in a side view of the wrist wearable biometric monitoring device embodiment of FIG. 1A.

FIG. 2A illustrates an exemplary layout of linear configurations including light processing elements of the PPG optical sensor aligned with light pass-through sections of a skin contacting surface of the housing of the device embodiment of FIG. 1A for producing per axis measurements.

FIG. 2B illustrates another exemplary layout of a linear configuration including light processing elements of the PPG optical sensor aligned with light pass-through sections of the skin contacting surface of the housing of the device for producing per axis measurements.

FIG. 2C illustrates yet another exemplary layout of linear configurations including light processing elements of the PPG optical sensor aligned with light pass-through sections of the skin contacting surface of the housing for producing per axis measurements.

FIG. 2D illustrates yet another exemplary layout of linear configurations including light processing elements of the PPG optical sensor aligned with light pass-through sections of the skin contacting surface of the housing for producing per axis measurements.

FIG. 2E illustrates yet another exemplary layout of a linear configuration including light processing elements of the PPG optical sensor aligned with light pass-through sections of the skin contacting surface of the housing of the device for producing per axis measurements.

FIG. 2F illustrates yet another exemplary layout of linear configurations including light processing elements of the PPG optical sensor aligned with light pass-through sections of the skin contacting surface of the housing for producing per axis measurements.

DETAILED DESCRIPTION

Figure 3A:
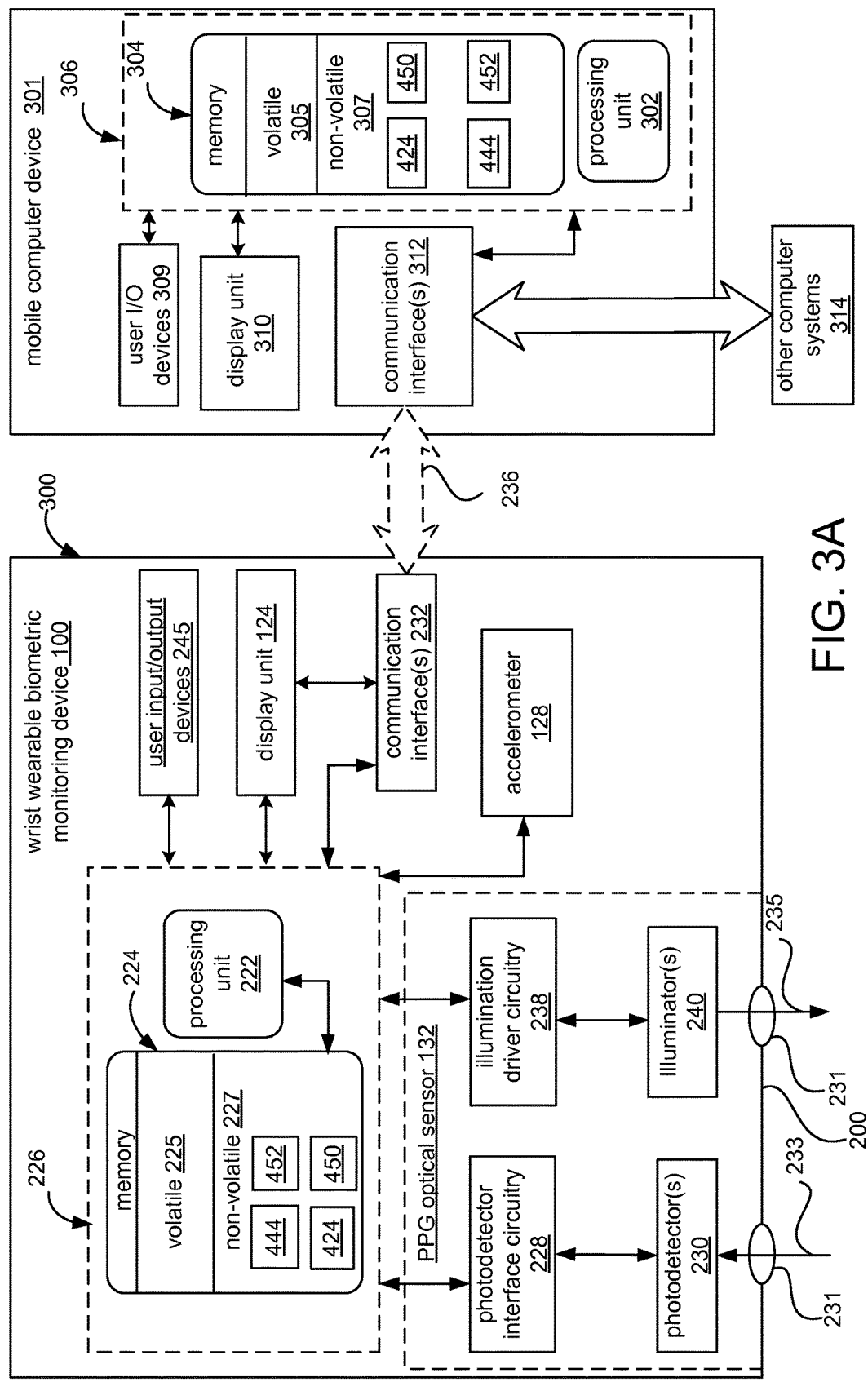
FIG. 3A is a block diagram of an embodiment of a system from a hardware perspective for active motion artifact compensation of heart rate data based on heart rate and accelerometer measurements taken along at least one shared axis of orientation.

The technology provides for one or more embodiments of a wearable sensor system for providing heart rate measurement per axis of orientation shared between a linear configuration of light processing elements of a photoplethysmography (PPG) optical sensor and an accelerometer. Each linear configuration of light processing elements includes at least one illuminator and at least one photodetector.

The wearable sensor system may be embodied in a device having a wrist watch or smart watch form factor like a wrist wearable biometric monitoring device. The wrist is the carpus or joint between the forearm and the hand. The wrist also has a readily identifiable neurovascular structure including as primary pulsatile components the radial and ulnar arteries. Embodiments of a wrist contact PPG optical sensor can detect small variations in the diameter of capillaries, arterioles or both in the wrist based on changes in one or more reflected signals detected by at least one photodetector of the PPG optical sensor.

As mentioned above, motion of the user during an activity, e.g. a cadence with walking or biking, can create motion artifact data in the same frequency range, e.g. beats per minute, and within an amplitude range, as expected for the heart rate data from the sensor, thus adversely affecting heart rate data accuracy. Even for a heart rate sensor positioned on a wrist, the movement of the user's legs during activities biking still creates motion artifacts in the heart rate measurements produced.

Measuring and correlating the heart rate data and the accelerometer data on a per axis basis, which is a per direction basis, provides more distinct or identifiable signals and therefore more precise data points. For example, in a frequency spectrum, an amplitude for a motion vector resulting from combined components of planar axes, e.g. a vector having x and y components, may be lower than an amplitude derived for the y component alone. The higher amplitude of the y component may exceed a floor amplitude, particularly in a weak signal, than a lower amplitude of a resultant vector of x and y or x, y and z components. Per axis measurement and correlation is particularly helpful when the PPG optical sensor is providing weak signals from the photodetectors.

Accelerometers which provide data from which acceleration, speed and motion for three (3) orthogonal axes of orientation with a common origin are commonly available. The skin area of the wrist upon which a housing in a wrist watch or smartwatch form factor is typically supported is sufficiently planar or flat so that light processing elements of a PPG optical sensor can be arranged in lines with light path access through a planar surface of a housing supporting the accelerometer and PPG optical sensor. An example of such a planar surface is a planar bottom of a smartwatch or wrist watch case typically in contact with the dorsal side wrist skin of a user.

In some embodiments, an axis of the accelerometer can be oriented along a radial direction of the wrist, and a second orthogonal and co-planar axis be oriented along an axial direction of the wrist. In one example, two orthogonal lines of light processing elements of the PPG optical sensor can be positioned in the same housing, one line sharing the accelerometer's axis of orientation for the radial direction of the wrist, and the other line sharing the accelerometer's axis of orientation in the axial direction of the wrist. In some embodiments (see FIG. 1B below) a predetermined origin, such as a center of a line of light processing elements, can be vertically aligned with the origin of the axes of the accelerometer for achieving a type of shared orientation which is a precisely matching orientation between the axes of both types of sensor devices. However, per axis of shared orientation measurement and correlation of data can still be achieved if the origins have an offset between them but a line of light processing elements still shares a same orientation as its corresponding accelerometer axis because an accelerometer typically measures a change in motion. For example, a linear configuration can be parallel to the y axis of the accelerometer, and thus the parallel linear configuration and the y axis share a same orientation. A linear configuration may also share orientation by being aligned along the y axis of the accelerometer so that the configuration and the y axis overlap, but their origins are not aligned.

FIG. 1A illustrates a top view of an embodiment of a wrist wearable biometric monitoring device 100 comprising a wearable sensor system including a PPG optical sensor and an accelerometer, each providing measurements for an axis of shared orientation. Neither the accelerometer nor the PPG optical sensor is shown in this view but are illustrated in FIG. 1B (128, 132). Data from sensors on the device can be used for determining heart rate and other biological or biometric statistics such as calorie expenditure and activity based information such as distance and speed for a user wearing the device. The biometric monitoring device 100 in this example has a wristwatch or smartwatch form factor comprising a housing 101 and a wristband 110. The wristband 110 may be embodied in various ways, for example in a traditional wriststrap with a buckle and holes, a bracelet, or in a stretchable band.

The wrist wearable biometric monitoring device 100 further comprises user input devices such as the illustrated examples of mode select buttons 102, 104, and 105. For example, the different buttons may be used to select application modes such an exercise mode or to select display of different biometric data or activity related data on a display unit 124 under a transparent protective layer or cover 122. One or more of the mode buttons may also be selected to activate different operational modes, for example device specific modes like a power saving mode, a standalone operation mode, or a network mode in which the biometric monitoring device 100 communicates with another computer system. In other examples, the one or more mode buttons can be used to input user-specific physiological parameters such as age, gender, height, weight, body mass index or maximum rate of oxygen consumption (VO2max).

In the illustrated example, display unit 124 displays an example heart rate (HR) of 110 beats per minutes (bpm) in display region 106 and displays an exemplary amount of 600 calories expended in a time period such as in the current day in a display region 107, and displays a time of day (e.g., 1:25:00 pm) in another display region 108.

FIG. 1B illustrates an example of an arrangement of different layers of hardware supported by housing 101 in a side view of the wrist wearable biometric monitoring device embodiment of FIG. 1A. In this side view, an exemplary arrangement starting from the top comprises the transparent protective layer 122 above the display unit 124. Control unit electronics 126 and accelerometer 128 and a power supply unit 130 are layered beneath the display unit 124 and above the PPG optical sensor unit 132. Due to the position of the housing 101 by the wrist band 110, a surface 200 of the housing contacts the user's wrist 134 on the dorsal side, allowing positioning of the light processing elements over the radial artery, when worn in this example in a typical manner for a wrist watch form factor type of device. The surface 200 provides one or more light pass-through sections with which one or more light processing elements (e.g. an illuminator, a photodetector) can be aligned. In other embodiments of a wrist wearable device, a wristband may position the housing to provide a skin contacting surface for the palmar side of the wrist.

Various examples of linear configurations of light processing elements are described below in FIGS. 2A through 2F. Preferably, the origin of the orthogonal axes of the accelerometer is also vertically aligned with a respective predefined origin for each linear configuration embodied by the PPG optical sensor which are also orthogonal if more than one configuration is implemented. An example of such a predefined origin for each linear configuration may be a center point of surface 200. For example, the accelerometer 128 in the side view of FIG. 1B may be stacked with its origin directly above the center point of surface 200, and in the examples of FIGS. 2A through 2F, an origin of each shown linear configuration is the center of surface 200.

Before discussing the various examples of linear configurations illustrated in FIGS. 2A through 2F, some examples of features of the light processing elements are discussed. Each illuminator is positioned by the housing 101 to direct light out of the surface 200 in contact with the skin when worn, and each photodetector is positioned by the housing 101 to receive reflected light, so loss of light between the surface and the skin is significantly diminished and control of spatial separation of a plurality of illumination beams is unnecessary.

An illuminator may be implemented as a light emitting diode (LEDs) in some examples. In other examples, an illuminator may be implemented using a laser, for example a VCSEL. A photodetector may be implemented using a typical silicon photodetector. In some example, a spherical lens is placed in the skin contacting surface of the PPG optical sensor for each photodetector and each illuminator for collimating both transmitted and reflected photons, and the lens also provides a reliable contact with the skin. Additionally, within the spherical lens or between the spherical lens and the photodetector, a wavelength selective filter can be arranged which filters incoming light to pass light about the wavelength transmitted by the at least one illuminator collinear with the photodetector. In one example, the diameter of each spherical lens is 0.8 mm. Additionally, the spherical lenses for the photodetectors and the illuminators can be surrounded at their edges with a light-blocking potting compound which further prevents optical leakage through air or perspiration. In some examples, the separation between a collinear photodetector and illuminator is between 1 mm and 5 mm.

Infrared and near infrared light such as about 850 nm may be transmitted by an illuminator of the PPG optical sensor for detection by one or more photodetectors of the PPG optical sensor. In many embodiments, an illuminator of the PPG optical sensor generates an optical signal about 550 nanometers (nm). Different sources give different wavelength ranges for the visible spectrum (e.g. ROYGBIV), but about 550 nm tends to be identified in the different sources as a shade of green near yellow. In any event, blood tissue has a high absorption of light about 550 nm so that based on the timing of reflected signals received at the photodetectors, changes in the size dimensions of the microvascular blood vessels can be detected, and hence heart beat rate can be determined. The use of light about 550 nm also reduces discomfort due to heating of tissue, such as may occur with the use of infrared illumination.

FIG. 2A illustrates an exemplary layout of linear configurations including light processing elements of the PPG optical sensor 132 aligned with light pass-through sections of a skin contacting surface 200 of the housing 101 of the of the device embodiment of FIG. 1A for producing per axis measurements. The size and shape of the skin contacting surface 200 of the housing need not be implemented as shown, (e.g. a circular region) but can be varied, for example due to aesthetic or practical consideration in designing the housing 101.

The light pass-through sections 231 may simply be openings, but would typically have a protective layer which passes light at the predetermined wavelength. The protective layer may be flush with the surface 200 or extend slightly beyond the surface 200 for contacting skin. The light passing protective layer may include lenses like the spherical lenses mentioned above and a filter for each photodetector for the predetermined wavelength. In each of the embodiments of FIG. 2A through 2F, an edge of just one of the light pass-through sections is labeled 231 to avoid overcrowding the drawing. In the embodiments illustrated, each light processing element, whether illuminator or diode is aligned with a respective light pass-through section 231. In other embodiments, there may be a lesser number of light pass-through sections to which more than one light processing element is aligned for directing or receiving light, but each such section may be larger in area and still match the linear configuration of its aligned light processing elements. For example, in FIG. 2B, instead of three sections, a single rectangular section 231 may be aligned with the photodetectors 202a and 202c and the illuminator 201.

In the example of FIG. 2A, an illuminator 201 forms a first linear configuration with photodetectors 202a and 202c which are on opposite sides of illuminator 201. In this example, illuminator 201, at the center of surface 200, is aligned with the origin of axes of accelerometer 128 so that the linear configurations including illuminator 201 match the orientation of corresponding axes of the accelerometer in a parallel plane, e.g. a parallel plane above the PPG optical sensor 132. An accelerometer may be a three axis accelerometer; however, the measurements for even just one shared axis provided by the PPG optical sensor can be used to remove motion artifacts from heart rate data. Continuing with the example of FIG. 2A, illuminator 201 is also flanked in a collinear configuration with photodetectors 202b and 202d forming a second shared axis of orientation with the accelerometer 128. In these examples, the linear configurations have matching orientations with the accelerometer axes of a parallel plane due to the alignment of the their origins. A matching orientation is a type of shared orientation. The first and second shared axes of orientation are orthogonal and in the same plane, also referred to as coplanar.

FIG. 2B illustrates another exemplary layout of a linear configuration including light processing elements of the PPG optical sensor 132 aligned with light pass-through sections of the skin contacting surface 200 for producing per axis measurements. In this example, the linear configurations of FIG. 2A are modified to include just one linear configuration of illuminator 201 and photodetectors 202a and 202c. Thus, the PPG optical sensor 132 measures reflected light in just one shared axis of orientation with the accelerometer 128.

FIG. 2C illustrates yet another exemplary layout of linear configurations including light processing elements of the PPG optical sensor 132 aligned with light pass-through sections of the skin contacting surface of the housing for producing per axis measurements. In this example, there are also two orthogonal linear configurations of light processing elements for directing light to and receiving reflections from skin in contact with surface 200 which correspond to or share axes of orientation with the accelerometer 128. A first linear configuration is formed by illuminator 201 and photodetector 202c, and a second linear configuration is formed by illuminator 201 and photodetector 202d. The first and second shared axes of orientation are orthogonal and in the same plane, also referred to as coplanar. The linear configurations of the PPG optical sensor in this example are not as co-extensive with the shared axes of the accelerometer 128, but the measurements by the photodetectors 202c and 202d still provide useful data for active compensation of motion artifacts.

Again, in this example, an illuminator 201 is aligned with the origin of axes of accelerometer 128 so that the linear configurations including illuminator 201 match the orientation of corresponding axes of the accelerometer in a parallel plane, e.g. a parallel plane above the PPG optical sensor 132.

FIG. 2D illustrates yet another exemplary layout of linear configurations including light processing elements of the PPG optical sensor aligned with light pass-through sections of the skin contacting surface of the housing for producing per axis measurements. The example layout in FIG. 2D is similar to the layout example of FIG. 2A except that a photodetector 212 forms a first linear configuration with illuminators 211a and 211c which are on opposite sides of photodetector 212 which shares a first axis of orientation with accelerometer 128. In this example, photodetector 212 is aligned with the origin of axes of accelerometer 128. Photodetector 212 is also flanked in a collinear configuration with illuminators 211b and 211d forming a second shared axis of orientation with the accelerometer 128. Again, the first and second shared axes of orientation are orthogonal and in the same plane, also referred to as coplanar.

However, unlike the arrangements in FIGS. 2A, 2B and 2C, the sets of collinear illuminators in FIG. 2D, for example a set including illuminators 211a and 211c and another set including illuminators 211b and 211d alternate their illumination in time so that the photodetector 212 alternately captures reflected light for each shared axis.

Alternating illumination between the different sets of illuminators in the example of FIG. 2D is an example of time division multiplexing. In other examples, frequency division multiplexing may be used in linear configurations having more than one illuminator so a photodetector signal can identify from which line the light detected was generated. In other words, reflected light generated from different linear configurations representing axes sharing orientation with corresponding axes of the accelerometer may be distinguished based on frequency division multiplexing. In the example of FIG. 2D, the set of illuminators 211a and 221c can each generate a first wavelength, e.g. 550 nm, and the other set of illuminators 211b and 211d can each generate a second wavelength, e.g. 850 nm. The photodetector 212 can be selected or filtered to have sensitivity to a carrier frequency. Each illuminator's illumination is modulated onto the carrier frequency, e.g. by a mixer such as may be included in control circuitry for the illuminator, for example the illustrated illumination driver circuitry 238 described below. Circuitry for processing the photodetector detection signals, for example the photodetector interface circuitry 228 described below, includes a demodulator, which can be a mixer as well, but this time for removing the carrier signal and filtering the resultant detections signals for each of the first and second wavelengths from which per axis measurements can be derived at the same time. By using frequency division multiplexing, the illuminators in the different linear configurations can provide illumination at the same time.

FIG. 2E illustrates yet another exemplary layout of a linear configuration including light processing elements of the PPG optical sensor aligned with light pass-through sections of the skin contacting surface of the housing of the device for producing per axis measurements along a shared axis of orientation with an accelerometer. In this example, the linear configurations of FIG. 2D are modified to include just one linear configuration of photodetector 212 and illuminators 211a and 211c. As the linear configuration shares just one axis of orientation with the accelerometer 128, the illuminators 211a and 211c can provide illumination at the same time. Illumination can be alternated if further measurements along the axis including the photodetector 212 as an origin, but in opposite directions along the axis are desired. In FIG. 2E, like in FIG. 2B, the PPG optical sensor 132 measures reflected light in just one shared axis of orientation with the accelerometer 128.

FIG. 2F illustrates yet another exemplary layout of linear configurations including light processing elements of the PPG optical sensor aligned with light pass-through sections of the skin contacting surface of the housing for producing per axis measurements. In this example, the photodetector 212 is aligned with the origin of axes of accelerometer 128 so that the linear configurations including photodetector 212 match the orientation of corresponding axes of the accelerometer in a parallel plane, e.g. a parallel plane above the PPG optical sensor 132. A first linear configuration is formed by illuminator 211c and photodetector 212, and a second linear configuration is formed by illuminator 211d and photodetector 212. Like the example in FIG. 2C, the linear configurations of the PPG optical sensor in this example are not as co-extensive with the shared axes of the accelerometer 128, but the measurements still provide useful data for active compensation of motion artifacts. However, like the example shown in FIG. 2D, each of the illuminators 211c and 211d alternate their illumination in time so that the photodetector 212 alternately captures reflected light for each shared axis.

The shapes of the pictorial representations of the light pass-through sections for the photodetectors and illuminators in FIGS. 2A through 2F are for illustrative purposes and can be varied.

FIG. 3A is a block diagram of an embodiment of a system 300 from a hardware perspective for active motion artifact compensation of heart rate data based on heart rate and accelerometer measurements taken for at least one shared axis of orientation. This system embodiment is described for illustrative purposes in the context of the wrist wearable biometric monitoring device 100 of FIG. 1A. However, the system may be implemented in other skin contact devices in which an accelerometer and light processing elements of a PPG optical sensor have at least one shared axis of orientation.

In the illustrated embodiment, active compensation of motion artifacts in heart rate data and heart rate determination based on compensated heart data may be performed locally within the monitoring device 100 or processing for the active compensation and heart rate determination may be shared with other computer systems. As shown, the wrist wearable biometric monitoring device 100 is communicatively coupled to a computer system like system 306 in mobile computer device 301 or another computer system 314 over a communication network connection 236.

In the illustrated example of FIG. 3A, the system embodiment 300 illustrated within the example of the wrist wearable biometric monitoring device 100 includes a computer system 226 including a processing unit 222 including one or more central processing units (CPU), processor or microcontrollers or a combination of these and a memory 224 for storing software and data. The memory 224 which may include volatile memory 225 (such as RAM), non-volatile memory 227 (such as ROM, flash memory, etc.) or some combination of the two. Some examples of software applications which may be stored in memory 224 and executed by the processing unit 222 are a motion determination module 424, an active motion artifact compensation module 444, a heart rate determination module 452, and other applications 450, e.g. a calorie expenditure application. Modules 424 and 444 will be discussed further in reference to the system embodiment 400 of software architecture in accordance with the present invention as described for FIG. 4. To avoid overcrowding the drawing, various data generated including accelerometer measurement data and PPG measurement data as well as determined and intermediately determined motion and heart rate data may be stored in volatile memory 225, non-volatile memory 227 or both, e.g. as per a user request to an application executing in the processing unit 222.

Additionally, data such as heart rate and accelerometer measurements may be stored off the monitoring device 100 to a removable memory device or another computer system (e.g. 306, 314) by the processing unit 222 via one or more communication interfaces 232.

The one or more communication interface(s) 232 include one or more network interfaces and transceivers which allow the wrist wearable biometric monitoring device 100 to communicate with other computer systems wirelessly or through a wired connection. Input devices 245 like a touch screen of display unit 124, buttons on the housing 101 like 102, 104 and 105 shown in FIG. 1A, a microphone or camera and output devices 245 like indicators which light up or audio output devices, e.g. devices which beep, may also be supported on the housing 101 as well as display unit 124 may also communicate with the processing unit 222 and memory 224.

As illustrated the accelerometer 128 and the PPG optical sensor 132 both communicate with the processing unit 222. The processing unit 222 includes a clock which provides one or more timing signals which are used to synchronize operation or data reading of different system devices. For example, software executing in the processing unit 222 can synchronize data capture by or from photodetectors of the PPG optical sensor 132 and the accelerometer 128 for one or more axes of shared orientation.

In this embodiment, the PPG optical sensor 132 comprises hardware components of one or more illuminators 240, illumination drive circuitry 238, one or more photodetectors 230 and photodetector interface circuitry 228. The illumination drive circuitry 238 drives the one or more illuminators 240 with current or voltage under the control of the processing unit 222, for example in accordance with a timing signal generated by the processing unit 222 under control of software. Photodetector interface circuitry 228 is coupled to the one or more photodetectors 230 for converting their analog detection signals to digital data which are stored by the processing unit 222 in memory 224. Light 235 about a predetermined wavelength generated by the one or more illuminators is directed via a light pass-through section 231 through a surface 200 of the housing 101 for contacting the wrist when worn by a user. In this example, the surface 200 is also a surface of the PPG optical sensor. Reflected light 233 reaches the one or more photodetectors 230, preferably from contacted skin, via a light pass-through section 231.

FIG. 3A also illustrates one or more hardware components of an embodiment of a wearable sensory system for providing heart rate measurement per axis of shared orientation. These one or more hardware components include the accelerometer 128, and the PPG optical sensor 132 including the one or more illuminators 240, the illumination driver circuitry 238, the one or more photodetectors 230 and the photodector interface circuitry 228 as well a housing 101 supporting and positioning the accelerometer and the one or more configurations of light processing elements. Additionally the embodiment of a wearable sensor system comprises the processing unit 222 for providing one or more software controlled processors for time synchronizing data capture for each shared axis of orientation between the accelerometer 128 and the PPG optical sensor 132 for providing co-sampled measurements from both 128 and 132 for each shared axis. The wearable sensor system embodiment may also include a memory like 224 for storing measurement data and software for controlling data capture.

FIG. 3A also illustrates a mobile computer device 301 which may communicate with the system 300 for sharing processing for motion determination, heart rate determination, and active motion artifact compensation (see e.g. 424, 452, 444 stored in non-volatile memory 307), and downloading data like the compensated heart rate data for display or use by other applications 450.

In the illustrated example, the mobile computer device 301 also includes a computer system 306 with a processing unit 302 including one or more central processing units (CPU), processors, or microcontrollers or a combination of these and a memory 304 which may include volatile 305 and non-volatile 307 memory components. Similarly, the mobile computer device 301 includes one or more communication module(s) 312 which allow the mobile computer device to communicate with the wrist wearable biometric monitoring device 100 and other computer systems 314. The mobile computer device also include input and output (I/O) devices 309 like buttons, touchscreen or a keypad, pointing device, keyboard or the like and a display unit 310.

To avoid cluttering the drawings, a power supply and power bus or power line is not illustrated, but each of the system embodiments illustrated from a hardware perspective also includes or has access to a power supply.

The example computer systems illustrated in the figures include examples of computer readable storage devices. A computer readable storage device is also a processor readable storage device. Such devices may include volatile and nonvolatile, removable and non-removable memory devices implemented in any method or technology for non-transitory storage of information such as computer readable instructions, data structures, program modules or other data. Some examples of processor or computer readable storage devices are RAM, ROM, EEPROM, cache, flash memory or other memory technology, CD-ROM, digital versatile disks (DVD) or other optical disk storage, memory sticks or cards, magnetic cassettes, magnetic tape, a media drive, a hard disk, magnetic disk storage or other magnetic storage devices, or any other device which can be used to store data, but not including a propagating signal.

Figure 3B:
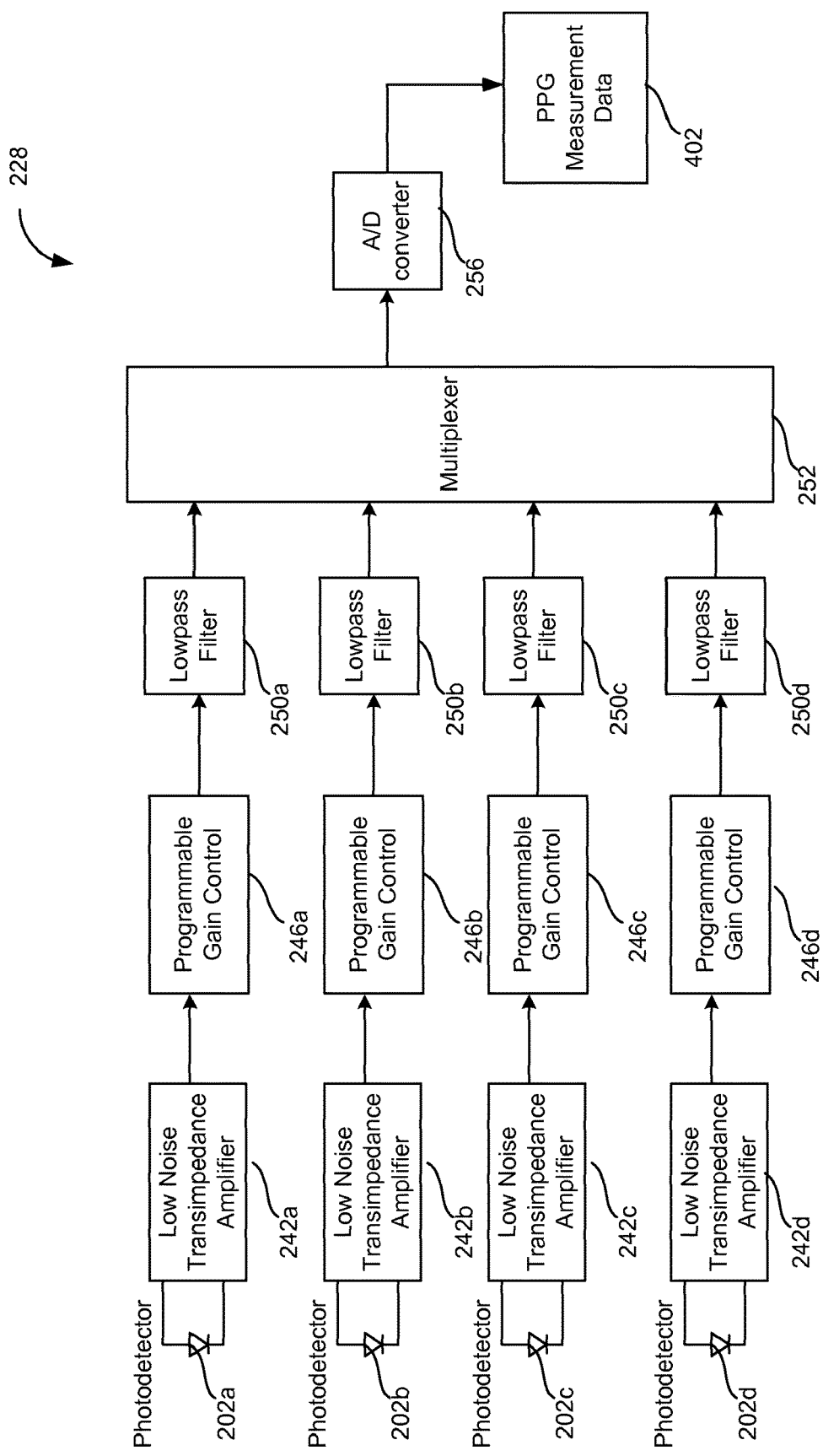
FIG. 3B is a block diagram of an architecture embodiment for photodetector interface circuitry interfacing with a photodetector of the PPG optical sensor.

FIG. 3B is a block diagram of an architecture embodiment for photodetector interface circuitry 228 interfacing with a photodetector of the PPG optical sensor. In this example, for contextual illustration, the photodetectors 202a, 202b, 202c, and 202d from the embodiment of FIG. 2A are referenced. Each of the photodetectors generates an electrical detection signal, for example a voltage or current, based on detected photons. A detection signal generated by each photodetector 202a, 202b, 202c, and 202d is received by a respective low noise transimpedance amplifier 242a, 242b, 242c and 242d which amplifies the signal.

Each amplified detection signal has its gain adjusted as necessary based on parameters stored for the programmable gain control 246a, 246b, 246c and 246d. Each amplified detection signal is then passed through a respective low pass filter 250a, 250b, 250c and 250d which has a higher frequency cutoff to maintain pulsatile components and remove high frequency components. In this example, a multiplexer 252 multiplexes signals from the different photodetectors 202a, 202b, 202c and 202d on different channels and multiplexes the use of the analog-to-digital converter 256 in generating digital data representing each detection signal as a PPG optical sensor measurement 402.

FIG. 3A has illustrated an embodiment of a wearable sensor system for providing per shared axis, co-sampled measurements from an accelerometer and a PPG optical sensor in a contextual example of a wrist wearable biometric monitoring device. Embodiments of the wearable sensor system may include devices placed on a different body part than the wrist; for example, the wearable sensor system may be embodied in a sensor pod form factor which can be placed on other body parts like the forehead, temple, ankle, upper arm, forearm, etc.

Figure 3C:
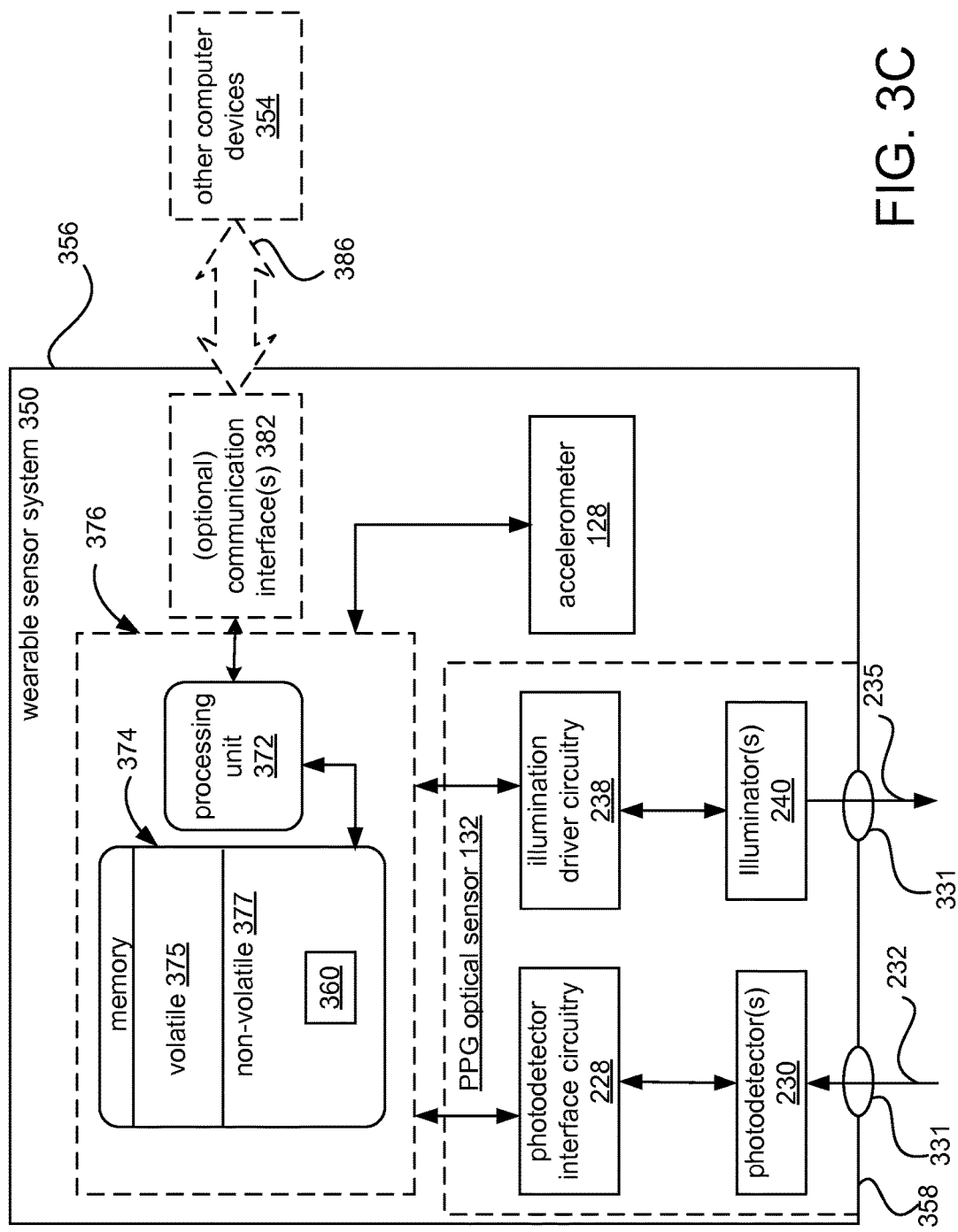
FIG. 3C is a block diagram of an embodiment of a wearable sensor system for providing heart rate measurements on per axis basis for each linear configuration of light processing elements of the PPG optical sensor forming an axis sharing an orientation with an axis of the accelerometer.

FIG. 3C is a block diagram of an embodiment of a wearable sensor system 350 for providing heart rate measurements on per axis basis for each linear configuration of light processing elements of the PPG optical sensor forming an axis sharing an orientation with an axis of the accelerometer. The illustrated embodiment of a wearable sensor system 350 comprises an accelerometer 128, and a PPG optical sensor 132 including the one or more illuminators 240, the illumination driver circuitry 238, the one or more photodetectors 230 and the photodector interface circuitry 228 as well a housing 356 supporting and positioning the accelerometer and the one or more configurations of light processing elements. The shape of housing 356 will vary based on practical factors like which body part the sensor system is attached to as well as aesthetics. In some examples, the housing 356 will have a form factor of a sensor pod. The housing 356 includes a surface 358, which like surface 200 in the embodiment of FIG. 3A, comprising one or more light pass-through sections 331 with which one or more light processing elements (e.g. an illuminator, a photodetector) can be aligned. The one or more light pass-through sections form linear configurations, preferably in a same plane provided by surface 358, so that light can be detected along each linear configuration, e.g. along the line the configuration forms. For illustration, light 235 of one or more predetermined wavelengths is being directed out of the one or more illuminators 240, and reflected light 232 is being received by the one or more photodetectors 230.

Additionally the embodiment of a wearable sensor system comprises a control unit 376 for providing one or more software controlled processors (e.g. a microcontroller with a clock in a stand alone wearable sensor system device like a sensor pod) for time synchronizing data capture for each shared axis of orientation between the accelerometer 128 and the PPG optical sensor 132, thus providing co-sampled measurements from both 128 and 132 for each axis formed by a linear configuration which shares the orientation of a corresponding axis of the accelerometer. The wearable sensor system embodiment may also include memory 374 which may have volatile memory 375 and non-volatile memory 377 storing measurement data and software 360 for controlling data capture when executing. Time stamps may be captured and stored for the accelerometer and PPG measurements under the control of software 360.

The illustrated embodiment also optionally includes one or more communication interfaces 382 for communicating with one or more other computer devices 354, which may use the measurement data for determining information by an application like a heart rate determination application. For example, if embodied in a sensor pod form factor, the wearable sensor system may relay the measurements wirelessly (e.g. Bluetooth) to a nearby device or be connected e.g. a USB port to another computer system for download of data. In another embodiment, the wearable sensor system operates in the context of a more sophisticated computer system (e.g. the wrist wearable biometric monitoring device 100) and relies on the processing unit, memory and perhaps communication interfaces of the embodying computer system for its operation.

Figure 3D:
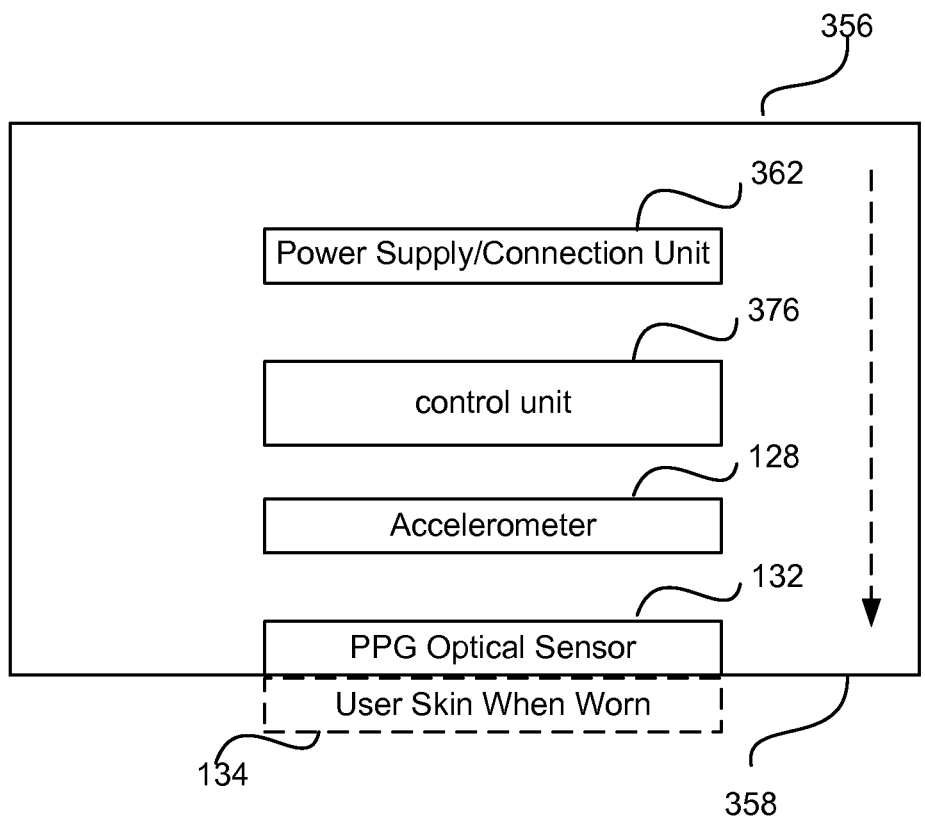
FIG. 3D illustrates an example of an arrangement of different layers of hardware supported by a housing for the wearable sensor system embodiment of FIG. 3C.

FIG. 3D illustrates an example of an arrangement of different layers of hardware supported by a housing 356 for the wearable sensor system embodiment of FIG. 3C. Starting from the surface 358 for contacting user skin 134 when worn, the illustrated example of a layout includes the PPG optical sensor 132, with its components like the illustrated examples 228, 230, 238 and 240, which shares surface 358 as its surface. The housing 356 positions the accelerometer 128 above the PPG optical sensor 132, preferably aligning the origin of the orthogonal axes of the accelerometer with an origin for the one or more linear configurations of light processing elements of the PPG optical sensor. Above the accelerometer in this example is the control unit 376 and a power supply unit of a unit for connecting to a power supply 362. Other hardware components may be added, even between the accelerometer and the PPG optical sensor, as long as the linear configurations and the axes of the accelerometer with which they share orientation are in parallel planes, and preferably with the origins aligned.

Figure 4:
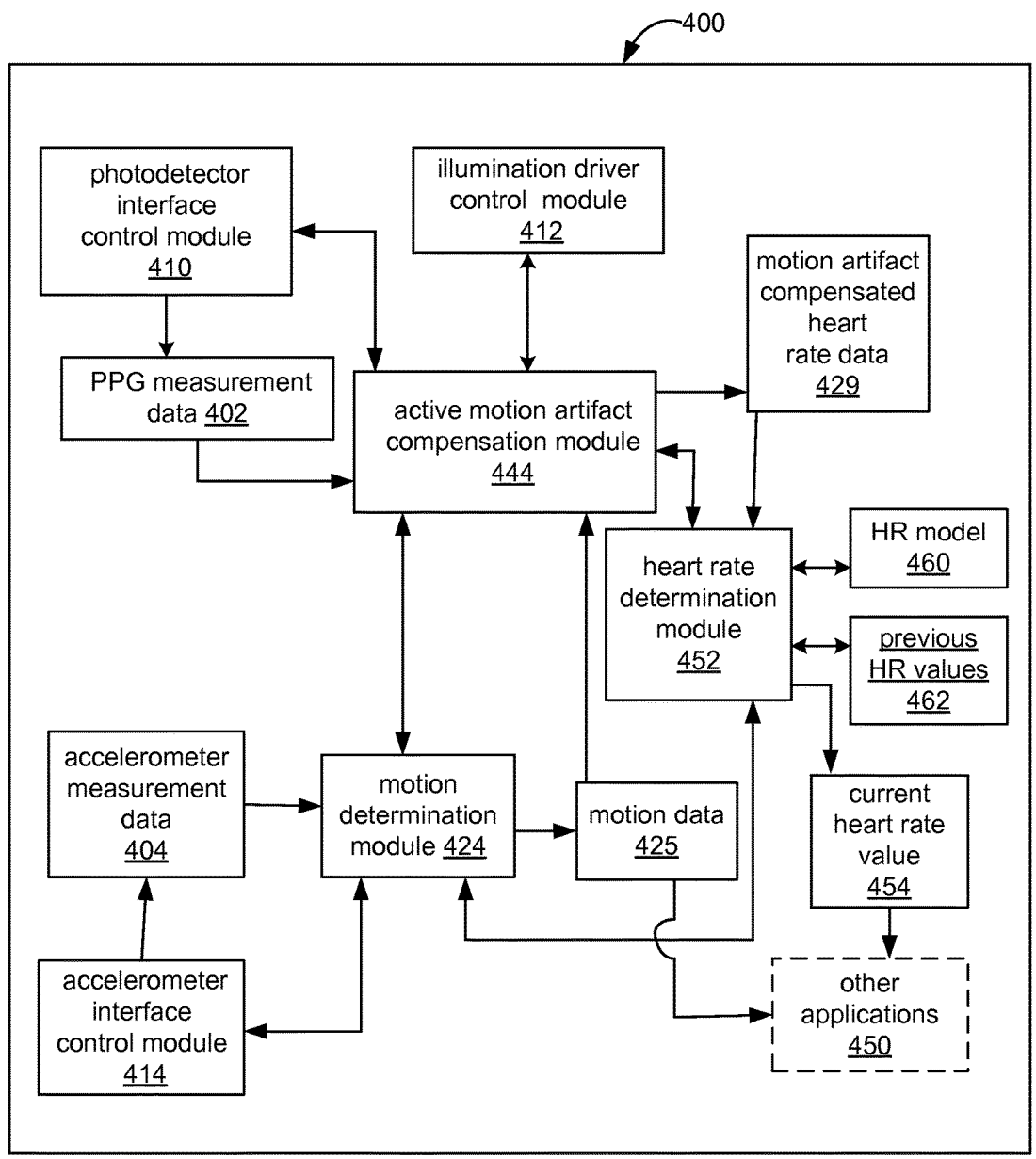
FIG. 4 is a block diagram of an embodiment of a system from a software perspective for heart rate data determination and active motion artifact compensation of heart rate data based on heart rate and accelerometer measurements taken along at least one shared axis of orientation.

FIG. 4 is a block diagram of an embodiment of a system 400 from a software perspective for active motion artifact compensation of heart rate data based on heart rate and accelerometer measurements taken for at least one shared axis of orientation. As mentioned above, the illustrated software system embodiment may be stored and executed in a computer system located in a wrist wearable biometric monitoring device 100 or the software system embodiment 400 may share processing with other communicatively coupled computer systems, e.g. computer system 306 of the mobile computer device 301.

In this example, a photodetector interface control module 410 executing on a processor (e.g. 222) time stamps the PPG measurement data 402, stores the digitally converted PPG measurement data 402, and notifies an executing (e.g. 222, 302) active motion artifact compensation software module 444 which reads the PPG measurement data 402.

In embodiments like those described in FIGS. 2D and 2F where there are two linear configurations corresponding to orientations of two axes of the accelerometer (e.g. 128) and wherein illuminators are arranged to share orientation rather than photodetectors as in FIGS. 2A and 2C, an illumination driver control module 412 may control the illumination driver circuitry 238 to alternate illumination between the linear configurations of illuminators representing respectively a first axis having a same orientation shared with a first axis of the accelerometer and a second axis having a same orientation shared with a second axis of the accelerometer. Time stamps for which axis was illuminated may also be stored for the generated PPG measurements 402. Additionally, in embodiments where illumination for making PPG measurement is generated periodically or on user demand rather than continuously, illumination time stamp data may also be used to correlate with time of capture of PPG measurement data 402.

Similarly, an accelerometer interface control module 414 executing on a processor (e.g. 222) stores the digital accelerometer measurement data 404 and notifies an executing (e.g. 222, 302) motion determination module 424 which reads the accelerometer measurement data 404. The accelerometer interface control module 414 time stamps the accelerometer measurement data 404. The motion determination module 424 determines and stores motion data 425 representing movement such as acceleration, along each axis of orientation measured by the accelerometer (e.g. 128).

The active motion artifact compensation module 444 communicates with the motion determination module 424 for time synchronizing data capture for each shared axis of orientation between the accelerometer and the PPG optical sensor. The time synchronization results in co-sampled, meaning sampled at the same time, measurement data from the accelerometer and the PPG optical sensor. Time synchronizing data capture for each shared axis may involve only identifying measurements generated at a same time as in a continuous operation mode using configurations like those in FIGS. 2A, 2B and 2C wherein the photodetectors extend in the axial directions. For periodic data capture or in embodiment like those of FIGS. 2D and 2F as discussed above, time synchronizing data capture for each shared axis may additionally involve turning on one or more illuminators for a shared axis in order to take the measurement for that axis. The co-sampling of measurement data allows for comparison between heart rate data determined from the PPG measurement data 402 and motion data determined from the accelerometer measurement data 404 for identifying data points satisfying a matching criteria. An example of a matching criteria is having the same frequency, e.g. beats per minute, for a PPG data point and an accelerometer data point derived from measurements taken at the same time or within a time threshold of each other.

The active motion artifact compensation module 444 generates heart rate data (not shown) based on the PPG measurement data, compares the determined heart rate data with the determined motion data 425, identifies heart rate data points satisfying a matching criteria with motion data points, and discards the identified data points from the heart rate data, so that the remaining heart rate data points make up the motion artifact compensated heart rate data 429 from which a current heart rate value 454 may be selected by the heart rate determination module 452.

Heart rate determination module 452 determines a current heart rate value 454 based on a cardiac or heart rate model 460, previous heart rate values 462 and the motion artifact compensated heart rate data 429. The current heart rate value 454 may be displayed for the user as in the example of FIG. 1A and other applications 450 may read the current heart rate value for their own processing.

An embodiment of the wearable sensor system may also include software and data components like the illustrated examples of the accelerometer interface control module 414, the accelerometer measurement data 404, the illumination driver control module 412, the photodetector interface control module 410, the PPG measurement data 402, and software for controlling time synchronization of data, for example software embodied in the motion determination module 424 and the active motion artifact compensation module 444 for this purpose.

The method embodiments are discussed for illustrative purposes in the context of the system embodiments discussed above. However, the method embodiments may also be practiced in other system embodiments as well.

Figure 5:
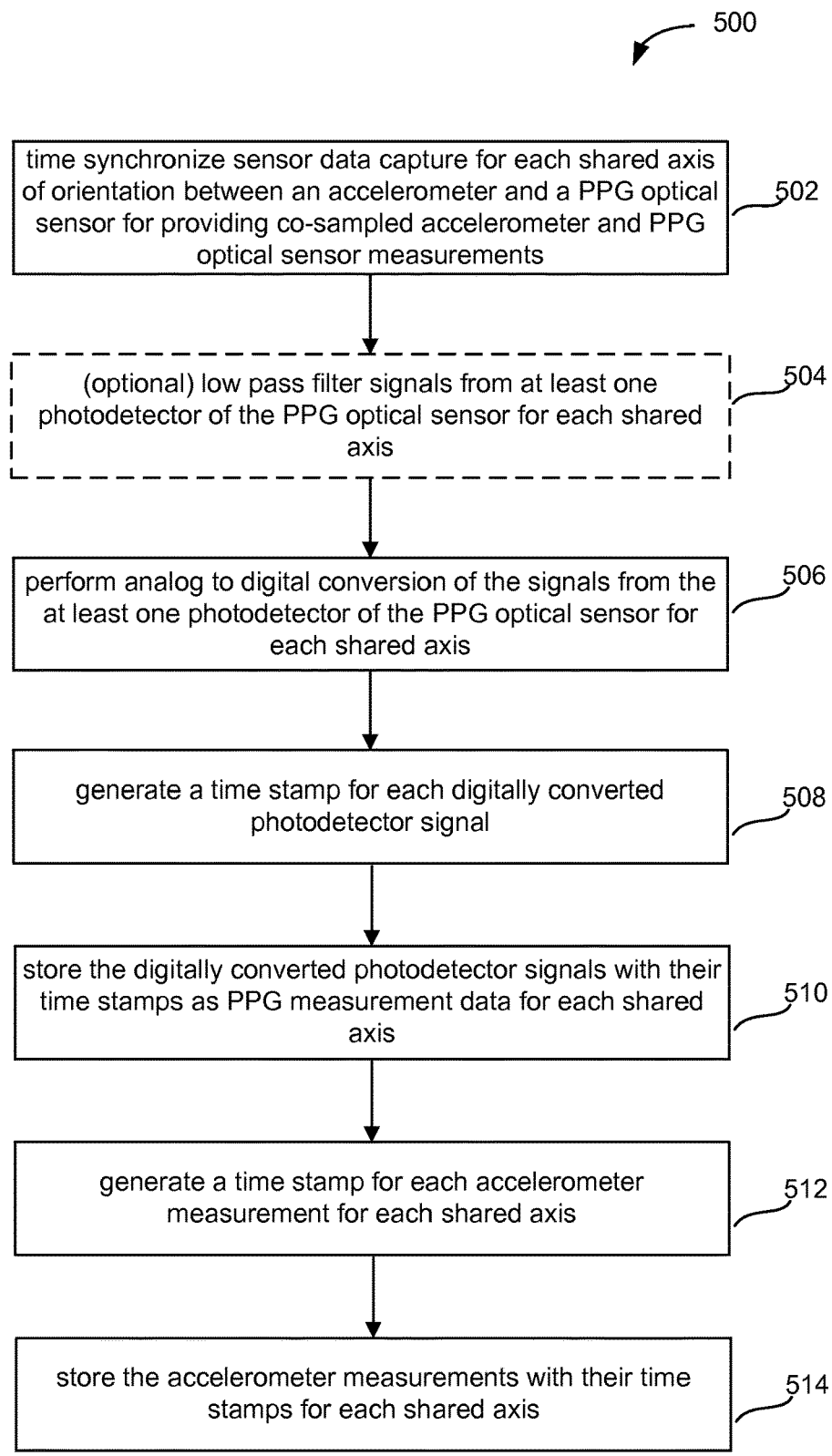
FIG. 5 is a flowchart of an embodiment of a method for obtaining co-sampled measurements from the accelerometer and the PPG optical sensor for each axis of orientation shared by the accelerometer and light processing elements of the PPG optical sensor.

FIG. 5 is a flowchart of an embodiment of a method for obtaining co-sampled measurements from the accelerometer and the PPG optical sensor for each axis of orientation shared by the accelerometer and light processing elements of the PPG optical sensor. In 502, sensor data capture for each shared axis of orientation between an accelerometer and a PPG optical sensor for providing co-sampled accelerometer and PPG optical sensor measurements is time synchronized. As discussed with respect to the embodiment of FIG. 4, the active motion artifact compensation module 444 can communicate with the motion determination module 424 for initiating time synchronization, for example based on a timing signal generated by a clock of the processing unit 222, of data capture for each shared axis of orientation between the accelerometer and the PPG optical sensor.

Photodetector analog signals representing measurements can optionally be low pass filtered as per step 504 in which signals from at least one photodetector of the PPG optical sensor for each shared axis are low pass filtered. In step 506, an analog-to-digital converter (e.g. 256) performs analog to digital conversion of the signals from the at least one photodetector of the PPG optical sensor for each shared axis.

A time stamp is generated for each digitally converted photodetector signal as per step 508. The digitally converted photodetector signals with their time stamps are stored as PPG measurement data for each shared axis. For example, the photodetector interface control module 410 may perform steps 508 and 510.

Additionally, a time stamp is generated for each accelerometer measurement for each shared axis, in other words on a per axis basis as per step 512, and the accelerometer measurements are stored (e.g. 404) with their time stamps in step 514. For example, the accelerometer interface control module 414 may perform steps 512 and 514. In many embodiments, an off-the-shelf accelerometer (e.g. 128) includes interface circuitry for processing its analog measurement signals and outputs data already in digital form for each axis of orientation. If desired and the analog signals were accessible in a type of accelerometer used, low pass filtering and analog to digital conversion may also be performed for the accelerometer data, for example by a hardware embodiment such as that shown in FIG. 3B.

The wearable biometric monitoring device like the wrist based device embodiment 100 illustrated in FIG. 1A may have different modes in which heart rate is automatically determined continuously, periodically or at other specified times as determined by a controlling application or based on a manual user action. For example, the user may touch an exercise mode button (e.g. 102) to indicate that a workout session is beginning in which case continuous heart rate measurements are desired. Or, in a free living application, the heart rate is determined automatically during periods of interest, such as when a significant amount of activity is detected based on accelerometer measurements.

Figure 6:
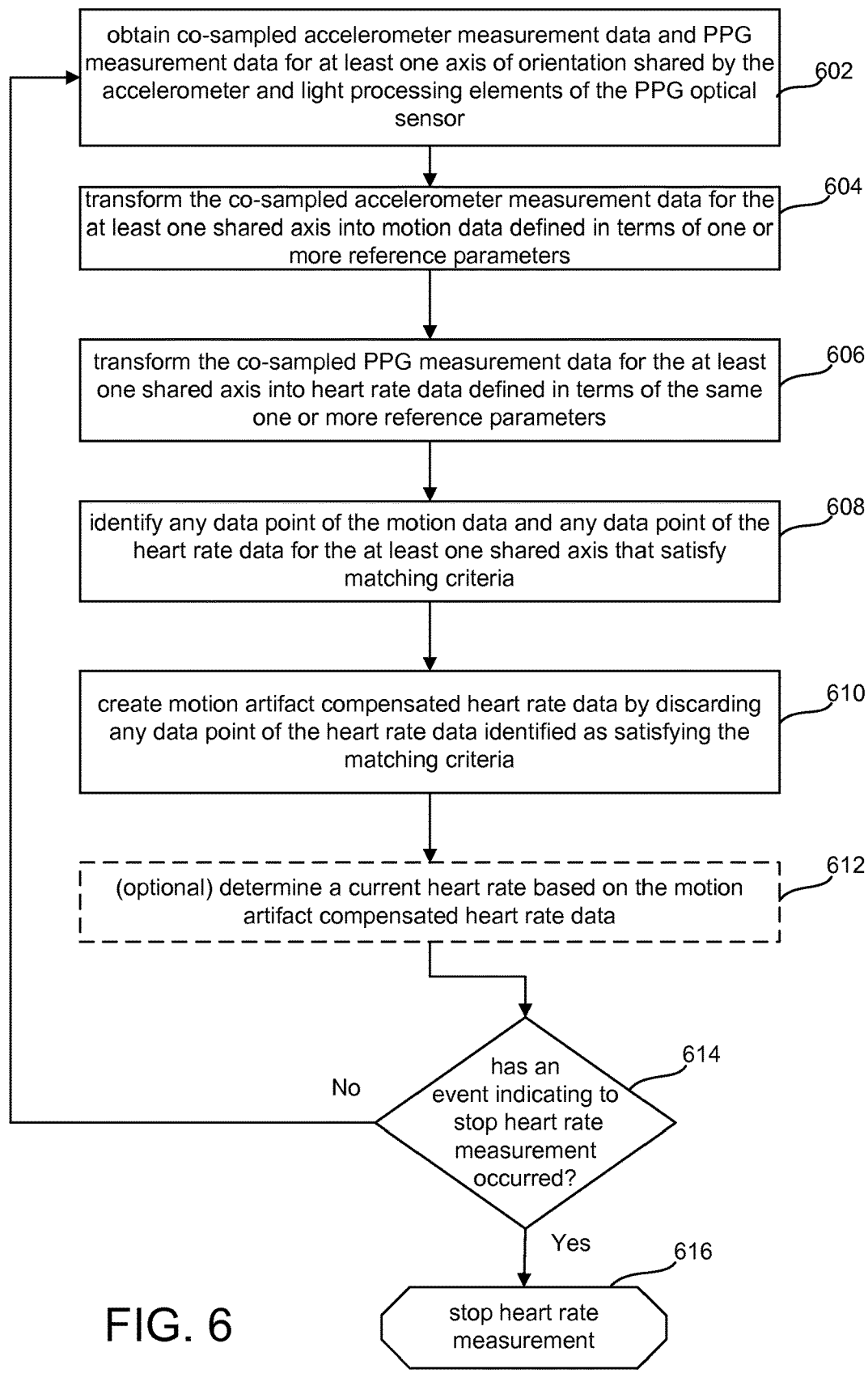
FIG. 6 is a flowchart of an embodiment of a method for active motion artifact compensation of heart rate data based on measurements taken for at least one axis of orientation shared by light processing elements of a PPG optical sensor and an accelerometer.

FIG. 6 is a flowchart of an embodiment of a method for active motion artifact compensation of heart rate data based on measurements taken for at least one axis of orientation shared by light processing elements of a PPG optical sensor and an accelerometer. In step 602 co-sampled accelerometer measurement data and PPG measurement data are obtained for at least one axis of orientation shared by the accelerometer and light processing elements of the PPG optical sensor (e.g. see the discussion above with respect to FIG. 5).

In step 604, software executing in a processing unit like the motion determination module 424 transforms the co-sampled accelerometer measurement data for the at least one shared axis into motion data defined in terms of one or more reference parameters. In step 606, software like the active motion artifact compensation module 444 transforms the co-sampled PPG measurement data for the at least one shared axis into heart rate data defined in terms of the same one or more reference parameters.

In step 608, executing software like the active motion artifact compensation module 444 identifies any data point of the motion data and any data point of the heart rate data for the at least one shared axis that satisfy matching criteria. An example of one or more reference parameters may be a measure of frequency like beats per minute. An example of matching criteria is being within a threshold of a same frequency. An identified heart rate data point which satisfies the matching criteria with motion data is being identified as a motion artifact.

In step 610, executing software like the active motion artifact compensation module 444 creates motion artifact compensated heart rate data by discarding any data point of the heart rate data identified as satisfying the matching criteria.

In step 612, optionally, a heart rate may be determined based on the motion compensated heart rate data. As per the example of FIG. 1A, heart rate readings may be displayed to a user, and in some embodiments, each displayed heart rate typically represents heart rate for a time window. However, the motion artifact compensated heart rate data may be used by various applications as an input for monitoring biometric parameters other than heart rate, for detecting the biometric monitoring device (e.g. 100) is being worn, or for determining activity related data.

Steps 602 through 610 represent an embodiment of a method for active motion artifact compensation of heart rate data for at least one axis of orientation shared by light processing elements of a PPG optical sensor and an accelerometer. For a continuous mode of operation, housekeeping steps 614 and 616 are also illustrated. In step 614, executing software like the active motion artifact compensation module 444 may receive a notification e.g. software interrupt, of an event indicating to stop heart rate measurement has occurred. For example, user input has indicated to stop continuous heart rate monitoring by requesting entry to a power saving mode. Responsive to notification of such an event, heart rate measurement is stopped in step 616, otherwise the processing repeats as new co-sampled measurement data is continuously obtained.

Figure 7:
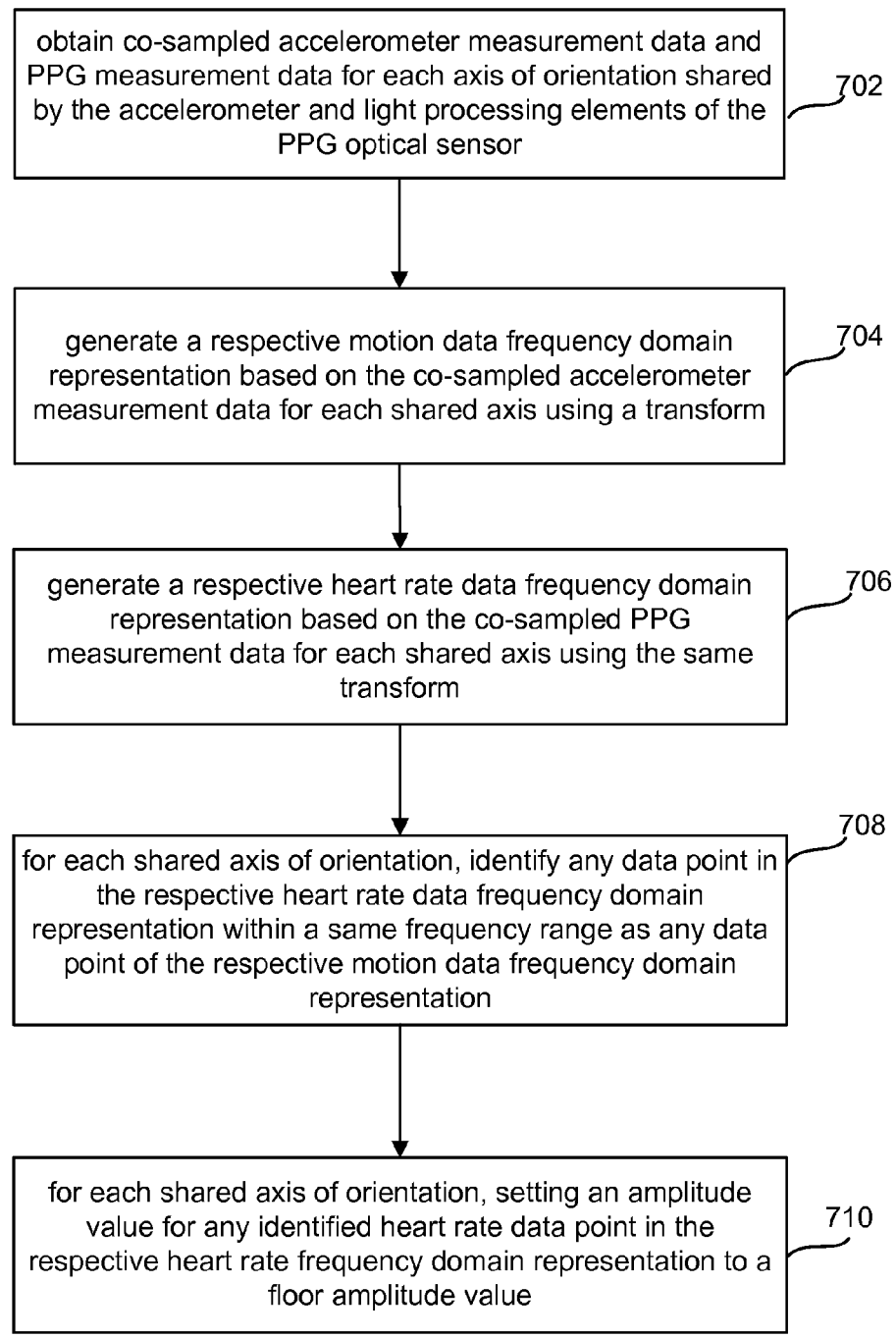
FIG. 7 is a flowchart of an embodiment of a method for active motion artifact compensation of heart rate data based on measurements taken for each axis of orientation shared by light processing elements of a PPG optical sensor and an accelerometer.

Before discussing a more detailed embodiment illustrated in FIG. 7, it is noted that for active compensation wherein data points are being actively identified and discarded, distinct measurement signals result in more precise measurement data, and thus make for easier identification of a heart rate data point which was actually generated due to movement by the user rather than blood volume change, and hence is a motion artifact. Alternatively, in embodiments wherein the PPG optical sensor records measurements along two orthogonal axes in the same plane (as does an accelerometer) co-sampled and co-planar axis components measured at the same time for the same type of data can be combined to form resulting direction vectors for each of the heart rate data and the motion data. For example, the directional vectors may be formed from the transformed data resulting in less data points. However, again a precision in values of the data points for axial components is diminished.

FIG. 7 is a flowchart of an embodiment of a method for active motion artifact compensation of heart rate data based on measurements taken for each axis of orientation shared by light processing elements of a PPG optical sensor and an accelerometer. In step 702, co-sampled accelerometer measurement data and PPG measurement data are obtained for each axis of orientation shared by the accelerometer and light processing elements of the PPG optical sensor.

In this embodiment frequency domain representations are generated based on the accelerometer measurements and the PPG measurements on a per axis basis. In one example of generating a frequency domain representation, for either motion data or heart rate data, measurement data (e.g. 402 or 404) may be accessed for a time window, such as the past few seconds, and a transform applied for calculating frequency domain values of the measurement data making up the representation, sometimes referred to as a signal or a spectrum. At least for each heart rate data representation, preliminary cleanup of the transformed data may be performed such as detecting one or more amplitude peaks in the representation, discarding peaks having an amplitude which does not exceed a floor amplitude threshold value, and discarding peaks having an amplitude exceeding a maximum amplitude value. The floor and maximum amplitude values may be determined for heart rate data based on a cardiac or heart rate model being used for determining a current heart rate value. An example of a transform that may be used is a type of Fourier transform like the Fast Fourier Transform (FFT) or the Discrete Fourier Transform (DFT).

In step 704, the motion determination module 424 generates a respective motion data frequency domain representation (e.g. frequency domain signal or spectrum) based on the co-sampled accelerometer measurement data for each shared axis using a transform. In step 706, the active motion artifact compensation module 444 generates a respective heart rate data frequency domain representation based on the co-sampled PPG measurement data for each shared axis using the same transform, for example the same FFT transform.

In an embodiment of the PPG optical sensor like that of FIG. 2A, there are two linear configurations sharing their orientations respectively with two axes of the accelerometer, a first axis formed by illuminator 201 and photodetectors 202a and 202c, and a second orthogonal and coplanar axis formed by illuminator 201 and photodetectors 202b and 202d. So two motion data frequency domain representations would be generated and two heart rate data frequency domain representations would be generated for data measured by the embodiment of FIG. 2A resulting in four frequency domain representations (e.g. signals or spectrums). If the accelerometer provides measurements distinguishing acceleration in opposite directions of an axis, for example in an X direction and a −X direction, it may be desirable to generate a frequency domain representation for each axis for each direction extending opposite from the illuminator 201, e.g. eight transforms.

In step 708, for each shared axis of orientation, the active motion artifact compensation module 444 identifies any data point in the respective heart rate data frequency domain representation which is within a same frequency range as any data point of the respective motion data frequency domain representation. For example, a same bin distribution may be applied to the resulting motion data and heart rate data representations or signals resulting from a same Fourier transform being applied. In one example, the active motion artifact compensation module 444 identifies any heart rate data point as being within a same frequency range that has a same bin as a motion data point in a corresponding motion data frequency domain signal for the same shared axis.

Step 710 illustrates of example of how to discard a heart rate data point satisfying matching criteria and thus having been identified as an artifact. In step 710, for each shared axis of orientation, the active motion artifact compensation module 444 sets an amplitude value for any identified heart rate data point in the respective heart rate data frequency domain representation to a floor amplitude value. The identified heart data point is effectively cancelled from the respective heart rate data frequency domain representation.

Figure 8A:
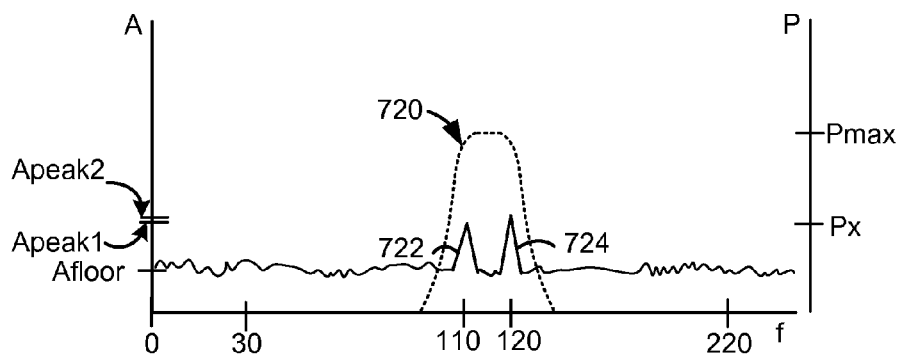
FIG. 8A illustrates an example frequency domain spectrum illustrating heart rate data prior to application of motion artifact compensation.

FIG. 8A illustrates an example heart rate frequency domain spectrum derived from heart rate measurements for a respective shared axis of orientation, with an accelerometer e.g. an x axis, prior to application of motion artifact compensation. The spectrum is plotted using an amplitude on the vertical axis (e.g. in terms of a voltage based unit and the scale may be logarithmic) and frequency (e.g., beats per minute) on the horizontal axis. The spectrum can be an amplitude spectrum or power spectrum, for instance. In this example, heart rates between 30 and 220 bpm are considered to be valid for the general human population. The noise floor NF represents the lowest possible amplitude (Afloor) of the spectrum.

A probability density function PDF 720 is illustrated in this example as a function of a continuous random variable which is the heart rate. A PDF describes the relative likelihood or probability for the random variable to take on a given value. The likelihood of the heart rate being a particular value is given by the height of the probability density function at that value. The PDF is plotted using a likelihood or probability P on the right vertical axis. In this example, the PDF is zero for frequencies less than 30 bpm and greater than 220 bpm, and rises up to a maximum probability of Pmax in the frequency range including data points illustrated as peaks 722 and 724. In this example, peak 722 represents measured heart rate or pulse data and has a frequency of 110 bpm. Peak 724 represents a motion artifact and has a frequency of 120 bpm. The probability that the heart rate would be 110 bpm is Px which is about the same probability that the heart rate would be 120 bpm. The PDF is not providing a basis for determining that the data point 724 representing a bpm of 120 is actually a motion artifact. However, comparison as per the method embodiments of FIG. 6 or 7 with a motion data frequency domain spectrum derived from co-sampled accelerometer measurements for the same shared axis of orientation (e.g. the x axis), if its spectrum plot were illustrated, would show a peak matching the amplitude and frequency of peak 724.

Figure 8B:
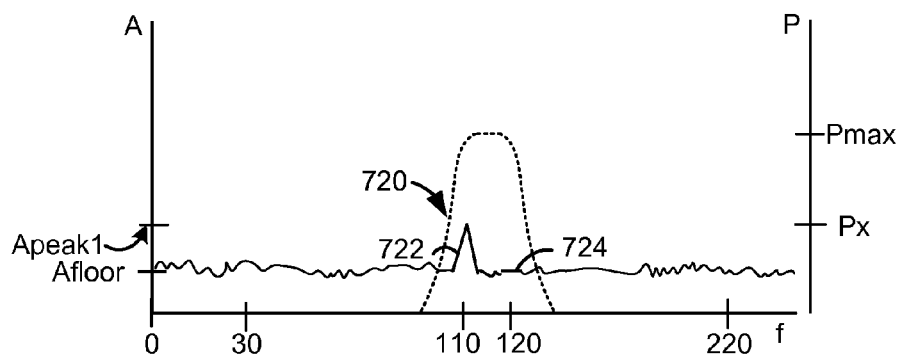
FIG. 8B illustrates the example frequency domain spectrum illustrating the heart rate data after application of motion artifact compensation.

FIG. 8B illustrates the example frequency domain spectrum illustrating the heart rate data after application of motion artifact compensation. Due to the identification of the matching motion data point for data point 724 in the heart rate data as illustrated by peak 724 in FIG. 8A, data point 724 would effectively be discarded by having its amplitude set to the amplitude floor, Afloor, in this example as illustrated by reference numeral 724 now that active motion artifact compensation has been applied.

Figure 9A:
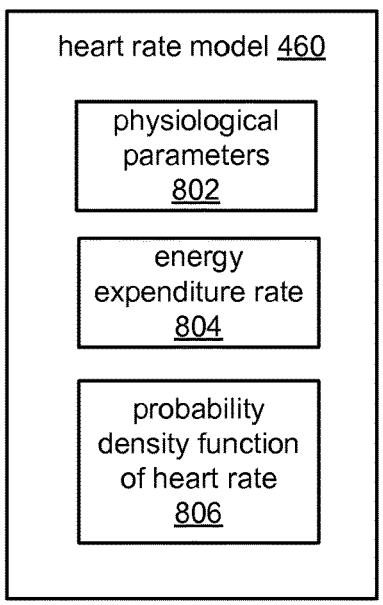
FIG. 9A illustrates an example of a heart rate model which may be used in determining a current heart rate value based on motion artifact compensated heart rate data.
Figure 9B:
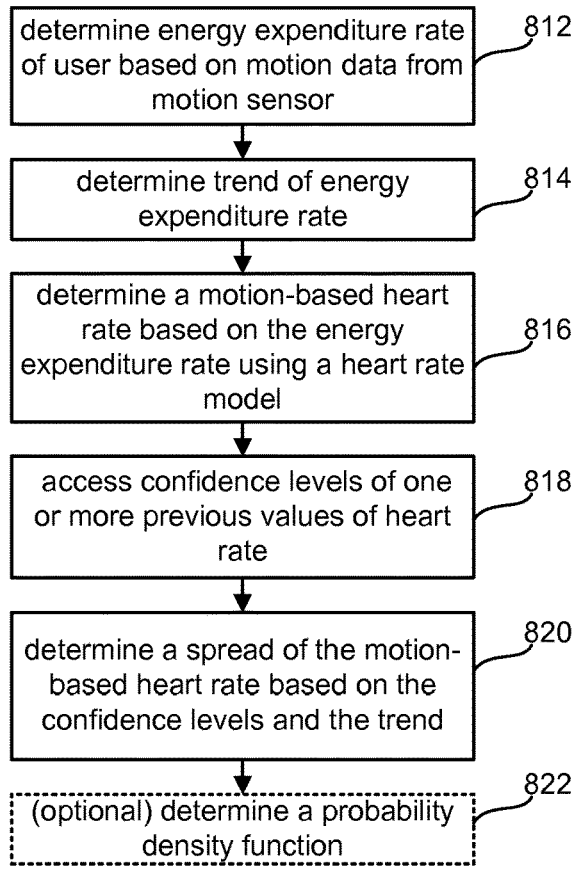
FIG. 9B depicts a flowchart of a process for determining a current heart rate estimate using the heart rate model of FIG. 9A for a time window

As mentioned in the discussion of FIG. 6 at optional step 612, a heart rate may be determined based on the motion artifact compensated heart rate data. FIGS. 9A and 9B disclose an embodiment of a heart rate model, sometimes also referred to as a cardiac model, and an embodiment of a method for determining a current heart rate value for display to user, use by other applications or both.

FIG. 9A illustrates an example of a heart rate model implemented as executable software and associated data and which may be used in determining a current heart rate value based on motion artifact compensated heart rate data. Executing software like the heart rate determination module 452 inputs motion data 425 or data derived from the motion data, other environmental data in some embodiments like ambient temperature, as well as heart rate values previously selected as current heart rate values 462 into the heart rate model 460 and receives as output an estimate of a current heart rate value. The heart rate determination module 452 as discussed further in the embodiment of FIG. 10 selects a current heart rate value between a measurement derived heart rate candidate determined from the motion artifact compensated heart rate data and the heart rate value estimated from the model.

Heart rate estimates based on the model acts as a validity check of the measured data, a sensor malfunction check, and covers periods when the PPG optical sensor is unable to provide data or only weak signals, e.g. due to temporarily losing contact with the skin. The heart rate model 460 is iteratively updated based on factors like changes in activity determined based on motion data and trends in measured heart rate data.

In the illustrated example, the heart rate model 460 stores physiological parameters 802 of the user for tailoring its heart rate estimate to the user. A current energy expenditure rate 804 such as a calorie burn rate can be determined based on the motion data 425 and the physiological parameters 802. In this example, the heart rate model 460 also stores a probability density function 806 for heart rate which has a spread and a center value. In this example, the probability density function (PDF) 806 is based on confidence levels (see discussion below) of previous heart rate values 462. Thus, the PDF acts as a data validity check as it defines a frequency range and an amplitude range in which the heart rate is expected to fall. Unfortunately, as noted above, motion artifacts tend to be in the same frequency and amplitude ranges defined by a PDF for heart rate.

FIG. 9B depicts a flowchart of a process for determining a current heart rate estimate using the heart rate model 460 for a time window (e.g. past few seconds). In step 812, the heart rate model 460 determines or updates an energy expenditure rate of the user based on motion data derived from the accelerometer 128. This can involve determining a type of activity the user is performing. In step 814, the heart rate model 460 determines a trend of the energy expenditure rate, e.g., steady, increasing or decreasing, for example based on energy expenditure rate data 804 stored in memory over a recent time period.

In step 816, the heart rate model 460 determines what is referred to as a motion based-heart rate which is a heart rate based on the energy expenditure rate and equations embodied in the heart rate model 460 software which relate heart rate to the energy expenditure rate. In this embodiment, the heart rate model 460 additionally provides a heart rate as a function of an energy expenditure rate (EER) and physiological parameters like gender, age and weight. In one example, the heart rate model 460 determines heart rate for women based on the following equation: a motion-based heart rate=(EER+20.4022+0.1263×weight−0.074×age)/0.4472. For men, the heart rate model 460 may determine heart rate using the following equation: a motion-based heart rate=(EER+55.0969−0.1988×weight−0.2017×age)/0.6309. The EER is in units of kJ/min, wherein 1 food calorie—4.2 kJ. These are just some examples of parameters and equations which may be used to determine a motion based heart rate.

In this embodiment, assigned confidence levels are stored with the previous heart rate values (e.g. 462), and in step 818 these confidence levels and associated previous values for a predetermined number of previous time windows are accessed. The previous values can encompass values selected from the motion artifact compensated heart rate data 429 as well as previously selected motion-based heart rate values which were calculated by the model. In one approach, the confidence level is available for the motion artifact compensated heart rate data 429 which is derived from actual measurements but not for the motion-based heart rate values calculated by the model. In another approach, a confidence level of a value calculated by the model is provided by an associated spread.

In step 820, a spread of the motion-based heart rate is determined based on the confidence levels of the one or more previous values of heart rate and the trend of the energy expenditure rate. The motion-based heart rate can be a center value of the spread. The spread indicates a range around the motion-based heart rate in which the actual heart rate is expected. The spread is an indication of a confidence level or an uncertainty of the motion-based heart rate. A higher spread indicates a higher uncertainty. In one approach, this step involves selecting a spread from among a plurality of predetermined spreads, for example predetermined spreads for different activities like biking, running, sleeping and the like.

Further, in one approach, when the trend of the energy expenditure rate is increasing or decreasing, the spread can be increased relative to the case where the trend is steady. In another approach, the spread is increased by different amounts for an increasing or decreasing trend. In another approach, the trend can include a degree of increasing or decreasing, and the spread can be increased by a relatively large amount when the degree of increasing or decreasing is relatively larger. The increase in the spread reflects an increased uncertainty in the heart rate when the heart rate is changing.

Optional step 822 determines a probability density function (PDF) of a heart rate from the model. The PDF may have a dispersion metric which is the spread. Further, the PDF may have a central value or central tendency which is a center of the spread. This central value may be the motion-based heart rate. The PDF can have a uniform shape in which the value of the PDF is either 0 or 1, or it can have a non-uniform shape. One example of a non-uniform shape is a shape with a peak and sides which slope downward from the peak.

The inputs to the model which are used to determine the PDF can include previous values of heart rate and associated confidence levels, energy expenditure rate (e.g., a current rate), and a trend of the energy expenditure rate. The PDF can be based on one or more previous values of heart rate by virtue of the heart rate model 460 identifying a correlation between energy consumption rate and heart rate based on the previous values of heart rate which were derived from measurement.

Figure 10:
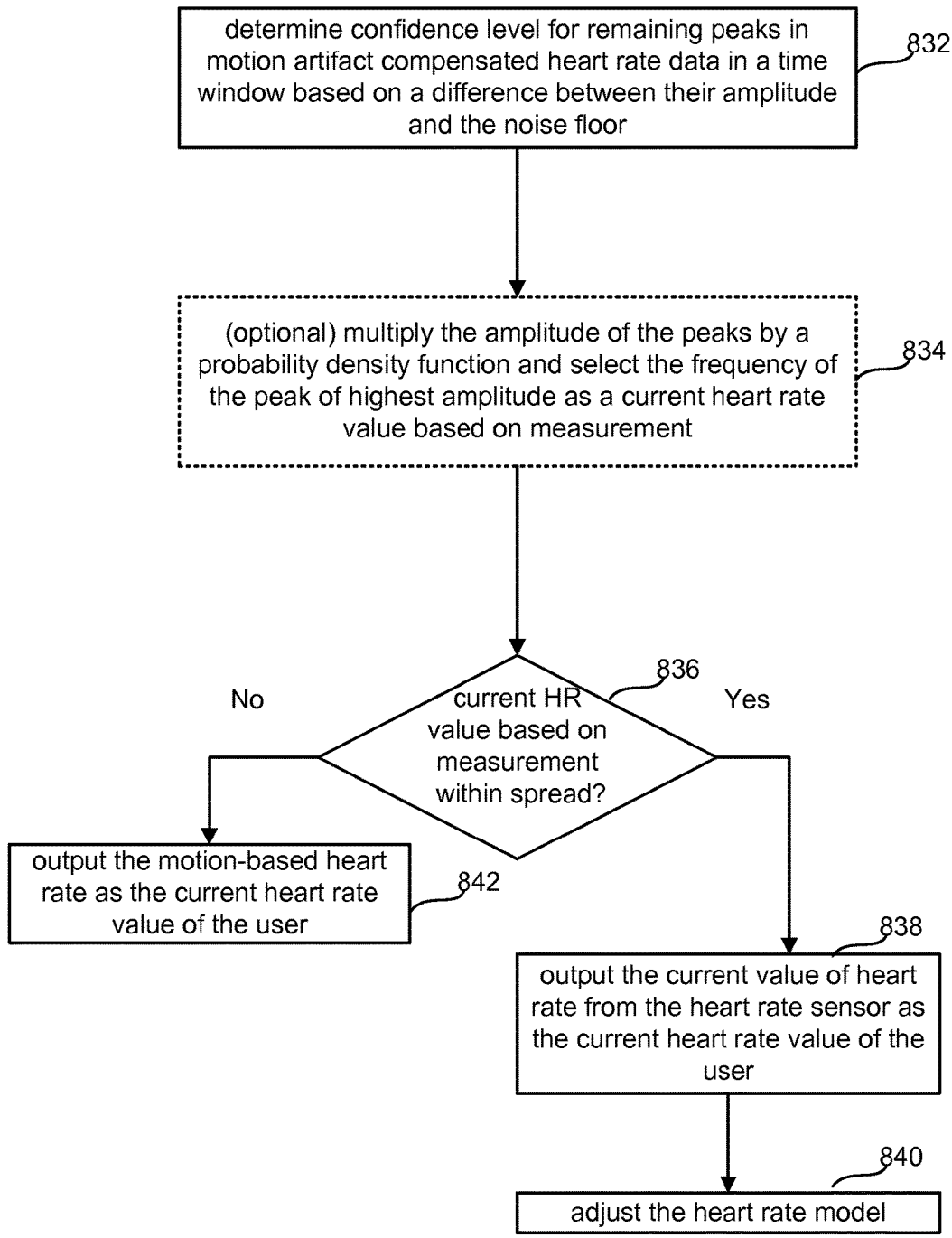
FIG. 10 is a flowchart of an embodiment of a method for determining a current heart rate value based on motion artifact compensated heart rate data and a heart rate model.

FIG. 10 is a flowchart of an embodiment of a method for determining a current heart rate value based on motion artifact compensated heart rate data and a heart rate model.

Step 832 involves determining a confidence level for remaining peaks based on a difference between their amplitude and the noise floor. Optional step 834 includes multiplying the amplitude of the peaks by a probability density function and selecting the frequency of the peak of highest amplitude as the current heart rate value based on measurement.

Next in decision step 836, the heart rate determination module 452 determines if the current heart rate (HR) value based on measurement is within the spread. If this is true, in step 838, the current heart rate value based on measurement is output as the current heart rate of the user. In other words, the current heart rate value based on measurement is within the expected range according to the model and is therefore passed through to the output. However, if the result of decision step 836 is false meaning the current heart rate value based on measurement is not within the spread, in step 842, the motion-based heart rate value is output as the current heart rate of the user. In other words, the current heart rate value based on measurement is not within the expected range according to the model, so the HR model 460 outputs a value it has calculated and which has a higher probability of being more correct. In step 840, the heart rate model 840 can adjust its parameters iteratively with changes detected in the heart rate values, for example in view of tracking a trend of the energy expenditure rate, increasing or decreasing.

Different manners of determining a current heart rate value are based on heart rate data derived from measurement and estimated by a HR model.

Additionally, although not typical as cadence and heart rate vary continuously, there can be times when a cadence from motion and the heart rate are in synch for an extended period of time. The active motion artifact compensation module 444 can identify that a predetermined number of data points that would be discarded for a predetermined time period, and if a threshold is exceeded, discontinue discarding heart rate data until the threshold is no longer exceeded.

An embodiment of a wearable sensor system for providing heart rate measurement per shared axis of orientation comprising: an accelerometer for providing accelerometer measurements for at least one accelerometer axis of orientation; a photoplethysmography (PPG) optical sensor having at least one linear configuration of light processing elements; a housing for supporting and positioning the accelerometer and the at least one linear configuration of light processing elements of the PPG optical sensor for the linear configuration to share the orientation of the at least one accelerometer axis of orientation; the housing having a surface with one or more light pass-through sections forming at least one linear configuration matching the at least one linear configuration of the light processing elements, and the housing aligning the light processing elements with the one or more light pass-through sections; and the surface with the one or more light pass-through sections is in contact with skin when the wearable sensor system is worn.

In another embodiment of the wearable sensor system described above, the wearable sensor system further comprises a wristband which supports the housing and positions the surface with the one or more light pass-through sections in contact with skin of the wrist.

In another embodiment of any of the wearable sensor systems described above, the wristband positions the surface with one or more light pass-through sections to be in contact with skin on a dorsal side of the wrist for sensing blood volume change in a radial artery.

In another embodiment of any of the wearable sensor systems described above, the surface with the one or more light pass-through sections is planar.

In another embodiment of any of the wearable sensor systems described above, the wearable sensor system further comprises one or more software controlled processors communicatively coupled to the accelerometer and the PPG optical sensor for time synchronizing data capture for each shared axis of orientation between the accelerometer and the PPG optical sensor for providing co-sampled measurements from the accelerometer and the PPG optical sensor.

In another embodiment of any of the wearable sensor systems described above, the housing for supporting and positioning the accelerometer and the at least one linear configuration of light processing elements of the PPG optical sensor for the linear configuration to share the orientation of the at least one accelerometer axis of orientation further comprises the housing aligning an origin of the at least one accelerometer axis of orientation with an origin of the at least one linear configuration of light processing elements.

In another embodiment of any of the wearable sensor systems described above, the accelerometer for providing accelerometer measurements for at least one accelerometer axis of orientation further comprises the accelerometer providing measurements for a first accelerometer axis and a second accelerometer axis, the first and second accelerometer axes being orthogonal and in a plane parallel to the surface with the one or more light pass-through sections; wherein the PPG optical sensor having at least one linear configuration of light processing elements further comprises the PPG optical sensor having a first linear configuration of light processing elements sharing the orientation of the first accelerometer axis and a second linear configuration of light processing elements sharing the orientation of the second accelerometer axis, the first and second linear configurations being orthogonal and co-planar; and the housing having the surface with the one or more light pass-through sections forming at least one linear configuration matching the at least one linear configuration of the light processing elements further comprises the surface having a first linear configuration of one or more light pass-through sections matching the first linear configuration of light processing elements and a second linear configuration of one or more light pass-through sections matching the second linear configuration of light processing elements, the first and second linear configurations of light processing elements being orthogonal and co-planar.

An embodiment of a method for active motion artifact compensation of heart rate data based on measurements taken for at least one axis of orientation shared by light processing elements of a photoplethysmography (PPG) optical sensor and an accelerometer comprises obtaining co-sampled accelerometer measurement data and PPG measurement data for at least one axis of orientation shared by the accelerometer and light processing elements of the PPG optical sensor; transforming the co-sampled accelerometer measurement data for the at least one shared axis of orientation into motion data defined in terms of one or more reference parameters; transforming the co-sampled PPG measurement data for the at least one shared axis of orientation into heart rate data defined in terms of the same one or more reference parameters; identifying any data point of the motion data and any data point of the heart rate data for the at least one shared axis of orientation that satisfy matching criteria; and creating motion artifact compensated heart rate data by discarding any data point of the heart rate data identified as satisfying the matching criteria.

In another embodiment of any of the method described above, the method further comprises determining a current heart rate value based on the motion artifact compensated heart rate data.

In another embodiment of any of the methods described above, the obtaining co-sampled accelerometer measurement data and PPG measurement data for at least one axis of orientation shared by the accelerometer and light processing elements of the PPG optical sensor further comprises obtaining co-sampled measurements from the accelerometer and the PPG optical sensor for the at least one axis of orientation shared by the accelerometer and at least two co-linear light processing elements of the PPG optical sensor in contact with skin of a user by time synchronizing data capture per shared axis of orientation by the accelerometer and the PPG optical sensor.

In another embodiment of any of the methods described above, the transforming the co-sampled accelerometer measurement data for the at least one shared axis of orientation into motion data defined in terms of one or more reference parameters further comprises generating a respective motion data frequency domain representation based on the co-sampled accelerometer measurement data for each shared axis using a transform; wherein transforming the co-sampled PPG measurement data for the at least one shared axis of orientation into heart rate data defined in terms of the same one or more reference parameters further comprises generating a respective heart rate frequency domain representation based on the co-sampled PPG measurement data for each shared axis using the same transform; and wherein identifying any data point of the motion data and any data point of the heart rate data for the at least one shared axis of orientation that satisfy matching criteria further comprises for each shared axis of orientation, identifying any data point in the respective heart rate data frequency domain representation satisfying matching criteria of being within a same frequency range as any data point of the respective motion data frequency domain representation; and wherein creating motion artifact compensated heart rate data by discarding any data point of the heart rate data identified as satisfying the matching criteria further comprises for each shared axis of orientation, setting an amplitude value for any identified heart rate data point in the respective heart rate frequency domain representation to a floor amplitude value.

In another embodiment of any of the methods described above, the method further comprises a same bin distribution is applied to the respective motion data frequency domain representation generated for each shared axis of orientation and to the respective heart data frequency domain representation generated for each shared axis of orientation; and wherein matching criteria of being within a same frequency range is satisfied by having a same bin.

An embodiment of a wrist wearable biometric monitoring device comprises an accelerometer for providing accelerometer measurements for at least one accelerometer axis of orientation; a photoplethysmography (PPG) optical sensor having at least one linear configuration of light processing elements; a housing for supporting and positioning the accelerometer and the at least one linear configuration of light processing elements of the PPG optical sensor for the linear configuration to share the orientation of the at least one accelerometer axis of orientation wherein the housing has a surface with one or more light pass-through sections forming at least one linear configuration matching the at least one linear configuration of the light processing elements, and the housing aligning the light processing elements with the one or more light pass-through sections, and the surface with the one or more light pass-through sections is in contact with skin when the wrist wearable biometric monitoring device is worn; and one or more processors communicatively coupled to the accelerometer and the PPG optical sensor for performing active motion artifact compensation of heart rate data based on measurements taken for at least one axis of orientation shared by the light processing elements of a photoplethysmography (PPG) optical sensor and the accelerometer.

In another embodiment of the wrist wearable biometric monitoring device described above, the one or more processors communicatively coupled to the accelerometer and the PPG optical sensor for performing active motion artifact compensation of heart rate data based on measurements taken for the at least one axis of orientation shared by the light processing elements of the photoplethysmography (PPG) optical sensor and the accelerometer further comprises the one or more processors obtaining co-sampled accelerometer measurement data and PPG measurement data for the at least one axis of orientation shared by the accelerometer and light processing elements of the PPG optical sensor; the one or more processors transforming the co-sampled accelerometer measurement data for the at least one shared axis of orientation into motion data defined in terms of one or more reference parameters; the one or more processors transforming the co-sampled PPG measurement data for the at least one shared axis of orientation into heart rate data defined in terms of same one or more reference parameters; the one or more processors identifying any data point of the motion data and any data point of the heart rate data for the at least one shared axis of orientation that satisfy matching criteria; and the one or more processors creating motion artifact compensated heart rate data by discarding any data point of the heart rate data identified as satisfying the matching criteria.

In another embodiment of any of the wrist wearable biometric monitoring devices described above, the wrist wearable biometric monitoring device further comprises a wristband which positions the surface with one or more light pass-through sections to be in contact with skin on a dorsal side of the wrist for sensing blood volume change in a radial artery.

In another embodiment of any of the wrist wearable biometric monitoring devices described above, the one or more processors communicatively coupled to the accelerometer and the PPG optical sensor time synchronize data capture for the at least one shared axis of orientation between the accelerometer and the PPG optical sensor for providing co-sampled measurements for the at least one shared axis of orientation from the accelerometer and the PPG optical sensor.

In another embodiment of any of the wearable sensor systems or in another embodiment of any of the wrist wearable biometric monitoring devices described above, the at least one linear configuration of light processing elements includes an illuminator co-linear with a photodetector.

In another embodiment of any of the wearable sensor systems or in another embodiment of any of the wrist wearable biometric monitoring devices described above, the at least one linear configuration of light processing elements includes an illuminator co-linear with a first photodetector and a second photodetector, the first and second photodetectors being on opposite sides of the illuminator.

In another embodiment of any of the wearable sensor systems or in another embodiment of any of the wrist wearable biometric monitoring devices described above, the at least one linear configuration of light processing elements includes a photodetector co-linear with a first illuminator and a second illuminator, the first and second illuminator being on opposite sides of the photo detector.

In another embodiment of any of the wearable sensor systems or in another embodiment of any of the wrist wearable biometric monitoring devices described above, the at least one linear configuration of light processing elements of the PPG optical sensor comprises a first linear configuration of light processing elements orthogonal to a second linear configuration of light processing elements; wherein the at least one accelerometer axis of orientation comprises a first accelerometer axis of orientation orthogonal to a second accelerometer axis of orientation; wherein the at least one linear configuration of one or more light pass-through sections comprises a first linear configuration of one or more light pass-through sections orthogonal to a second linear configuration of one or more light pass-through sections; the first linear configuration of light processing elements and the first linear configuration of one or more light pass-through sections share the orientation of the first accelerometer axis of orientation; and the second linear configuration of light processing elements and the second linear configuration of one or more light pass-through sections share the orientation of the second accelerometer axis of orientation.

In another embodiment of any of the wearable sensor systems or in another embodiment of any of the wrist wearable biometric monitoring devices described above, the at least one linear configuration of light processing elements of the PPG optical sensor comprises a first linear configuration of light processing elements orthogonal to a second linear configuration of light processing elements; wherein the at least one accelerometer axis of orientation comprises a first accelerometer axis of orientation orthogonal to a second accelerometer axis of orientation; wherein the at least one linear configuration of one or more light pass-through sections comprises a first linear configuration of one or more light pass-through sections orthogonal to a second linear configuration of one or more light pass-through sections; the first linear configuration of light processing elements and the first linear configuration of one or more light pass-through sections share the orientation of the first accelerometer axis of orientation; the second linear configuration of light processing elements and the second linear configuration of one or more light pass-through sections share the orientation of the second accelerometer axis of orientation; the first linear configuration of light processing elements comprises a first illuminator co-linear with a first photodetector and a second photodetector on an opposite side of the first illuminator than the first photodetector, the first and second photodetector capturing reflected light along a first axis of orientation shared with the accelerometer; and the second linear configuration of light processing elements comprises the first illuminator co-linear with a third photodetector and a fourth photodetector on an opposite side of the first illuminator than the third photodetector, the third and fourth photodetectors being orthogonal to the first and second photodetectors, the third and fourth photodetectors capturing reflected light along a second axis of orientation shared with the accelerometer.

In another embodiment of any of the wearable sensor systems or in another embodiment of any of the wrist wearable biometric monitoring devices described above, the at least one linear configuration of light processing elements of the PPG optical sensor comprises a first linear configuration of light processing elements orthogonal to a second linear configuration of light processing elements; wherein the at least one accelerometer axis of orientation comprises a first accelerometer axis of orientation orthogonal to a second accelerometer axis of orientation; wherein the at least one linear configuration of one or more light pass-through sections comprises a first linear configuration of one or more light pass-through sections orthogonal to a second linear configuration of one or more light pass-through sections; the first linear configuration of light processing elements and the first linear configuration of one or more light pass-through sections share the orientation of the first accelerometer axis of orientation; the second linear configuration of light processing elements and the second linear configuration of one or more light pass-through sections share the orientation of the second accelerometer axis of orientation; the first linear configuration of light processing elements comprises a first photodetector co-linear with a first illuminator and a second illuminator on an opposite side of the first photodetector than the first illuminator, the first and second illuminators generating light along a first axis of orientation shared with the accelerometer; and the second linear configuration of light processing elements comprises the first photodetector co-linear with a third illuminator and a fourth illuminator on an opposite side of the first photodetector than the third illuminator, the third and fourth illuminators being orthogonal to the first and second illuminators, the third and fourth illuminators generating light along a second axis of orientation shared with the accelerometer.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A wearable sensor system for providing heart rate measurement per shared axis of orientation, wherein the wearable sensor system is susceptible to motion artifacts that can adversely affect heart rate determinations, the system comprising:
    an accelerometer configured to provide accelerometer measurements for at least first and second accelerometer axes of orientation that are orthogonal to one another;
    a photoplethysmography (PPG) optical sensor having at least first and second linear configurations of light processing elements that are orthogonal to one another; and
    a housing configured to support and position the accelerometer and the first and second linear configurations of light processing elements of the PPG optical sensor so that the first linear configuration of light processing elements and the first accelerometer axis of orientation have a first shared axis of orientation, and the second linear configuration of light processing elements and the second accelerometer axis of orientation have a second shared axis of orientation;
    the housing having a surface with one or more light pass-through sections forming at least first and second linear configurations matching the at least first and second linear configurations of the light processing elements, and the housing aligning the first and second linear configurations of light processing elements with the first and second linear configurations formed by the one or more light pass-through sections;
    wherein the surface of the housing with the one or more light pass-through sections is configured to be in contact with skin of a user when the wearable sensor system is worn;
    wherein data captured for the first and second shared axes of orientation between the accelerometer and the PPG optical sensor are time synchronized to provide co-sampled measurements from the accelerometer and the PPG optical sensor; and
    at least one processor configured to
        transform the co-sampled accelerometer measurements for each of the first and second shared axes of orientation into respective motion data;
        transform the co-sampled PPG measurements for each of the first and second shared axes of orientation into respective heart rate data;
        for each shared axis of orientation, of the first and second shared axes of orientation, compare the respective motion data to the respective heart rate data to identify, based on the comparison therebetween, any data point of the respective motion data and any data point of the respective heart rate data for the shared axis of orientation that satisfy matching criteria;

for each shared axis of orientation, of the first and second shared axes of orientation, create respective motion artifact compensated heart rate data by discarding any data point of the respective heart rate data identified as satisfying the matching criteria; and determine a heart rate value based on the respective motion artifact compensated heart rate data for at least one of the first and second shared axes of orientation.

2. The wearable sensor system of claim 1 wherein the at least first and second linear configurations of light processing elements includes an illuminator co-linear with at least one of a first photodetector and a second photodetector, the first and second photodetectors being on opposite sides of the illuminator.

3. The wearable sensor system of claim 1 further comprising a wristband connected to the housing and configured to position the surface of the housing with the one or more light pass-through sections to be in contact with skin of a wrist when the wearable sensor system is worn.

4. The wearable sensor system of claim 3 wherein the wristband is configured to position the surface of the housing with one or more light pass-through sections to be in contact with skin on a dorsal side of a wrist to thereby enable sensing of blood volume change in a radial artery.

5. The wearable sensor system of claim 4 wherein the surface of the housing with the one or more light pass-through sections is planar.

6. The wearable sensor system of claim 1 wherein the housing is also configured to align an origin of at least one of the first and second accelerometer axes of orientation with an origin of at least one of the first and second linear configurations of light processing elements.

7. The wearable sensor system of claim 1 wherein the first and second accelerometer axes of orientation are in a plane parallel to the surface of the housing with the one or more light pass-through sections, and the first and second linear configurations of light processing elements are in a plane parallel to the surface with the one or more light pass-through sections.

8. The system of claim 1, wherein the respective motion data, for each of the first and second shared axes of orientation, is defined in terms of one or more reference parameters, and the respective heart rate data, for each of the first and second shared axes of orientation, is defined in terms of the same one or more reference parameters.

9. A method for use with a wearable sensor system that includes an accelerometer, a photoplethysmography (PPG) optical sensor, and a housing, the accelerometer configured to provide accelerometer measurements for at least first and second accelerometer axes of orientation that are orthogonal to one another, the PPG optical sensor having at least first and second linear configurations of light processing elements that are orthogonal to one another, and the housing configured to support and position the accelerometer and the first and second linear configurations of light processing elements of the PPG optical sensor so that the first linear configuration of light processing elements and the first accelerometer axis of orientation have a first shared axis of orientation, and the second linear configuration of light processing elements and the second accelerometer axis of orientation have a second shared axis of orientation, the housing having a surface with one or more light pass-through sections forming at least first and second linear configurations matching the at least first and second linear configurations of the light processing elements, and the housing aligning the first and second linear configurations of light processing elements with the first and second linear configurations formed by the one or more light pass-through sections, wherein the surface of the housing with the one or more light pass-through sections is configured to be in contact with skin of a user when the wearable sensor system is worn, the method for active motion artifact compensation of heart rate data based on measurements taken for at least the first and second axes of orientation shared by the light processing elements of the PPG optical sensor and the accelerometer, the method comprising:

obtaining co-sampled accelerometer measurement data and PPG measurement data for at least the first and second axes of orientation shared by the accelerometer and the light processing elements of the PPG optical sensor;

transforming the co-sampled accelerometer measurement data for each of the at least first and second shared axes of orientation into respective motion data defined in terms of one or more reference parameters;

transforming the co-sampled PPG measurement data for each of the at least first and second shared axes of orientation into respective heart rate data defined in terms of the same one or more reference parameters;

for each shared axis of orientation, of the first and second shared axes of orientation, identifying any data point of the respective motion data and any data point of the respective heart rate data that satisfy matching criteria; and for each shared axis of orientation, of the first and second shared axes of orientation, creating respective motion artifact compensated heart rate data by discarding any data point of the respective heart rate data identified as satisfying the matching criteria.

10. The method of claim 9 further comprising:

determining a heart rate value based on the respective motion artifact compensated heart rate data for at least one of the first and second shared axes of orientation.

11. The method of claim 9 wherein obtaining co-sampled accelerometer measurement data and PPG measurement data for the at least first and second axes of orientation shared by the accelerometer and light processing elements of the PPG optical sensor further comprising:

obtaining co-sampled measurements from the accelerometer and the PPG optical sensor for each of the at least the first and second axes of orientation shared by the accelerometer and at least two co-linear light processing elements of the PPG optical sensor in contact with skin of a user by time synchronizing data capture per shared axis of orientation by the accelerometer and the PPG optical sensor.

12. The method of claim 9 wherein:

the transforming the co-sampled accelerometer measurement data for each of the at least first and second shared axes of orientation into respective motion data defined in terms of one or more reference parameters includes generating a respective motion data frequency domain representation based on the respective co-sampled accelerometer measurement data for each shared axis using a transform;

the transforming the co-sampled PPG measurement data for each of the at least first and second shared axes of orientation into heart rate data defined in terms of the same one or more reference parameters includes generating a respective heart rate frequency domain representation based on the respective co-sampled PPG measurement data for each shared axis using the same transform; and the identifying any data point of the respective motion data and any data point of the respective heart rate data for each of the at least first and second shared axes of orientation that satisfy matching criteria includes for each shared axis of orientation, identifying any data point in the respective heart rate data frequency domain representation satisfying matching criteria of being within a same frequency range as any data point of the respective motion data frequency domain representation; and the creating the respective motion artifact compensated heart rate data for each of the at least first and second shared axes of orientation by discarding any data point of the heart rate data identified as satisfying the matching criteria includes for each shared axis of orientation, setting an amplitude value for any identified heart rate data point in the respective heart rate frequency domain representation to a floor amplitude value.

13. The method of claim 12 wherein:

a same bin distribution is applied to the respective motion data frequency domain representation generated for each shared axis of orientation and to the respective heart data frequency domain representation generated for each shared axis of orientation; and the matching criteria of being within a same frequency range is satisfied by having a same bin.

* * * * *